(12) United States Patent
Yuuki et al.

(10) Patent No.: US 7,348,170 B2
(45) Date of Patent: Mar. 25, 2008

(54) FUNGUS-ORIGIN LYSYL OXIDASES

(75) Inventors: Kensuke Yuuki, Kakamigahara (JP); Atsuki Toumoto, Kakamigahara (JP); Masayuki Machida, Tsukuba (JP); Keietsu Abe, Shiogama (JP); Katsuya Gomi, Sendai (JP); Kiyoshi Asai, Tokyo (JP); Motoaki Sano, Tsukuba (JP); Taishin Kin, Tokyo (JP); Hideki Nagasaki, Tokyo (JP); Akira Hosoyama, Tokyo (JP); Osamu Akita, Higashihiroshima (JP); Naotake Ogasawara, Ikoma (JP); Satoru Hisahara, Fukuoka (JP)

(73) Assignees: Amano Enzyme Inc., Nagoya-shi (JP); National Institute of Advanced Industrial Science and Technology, Tokyo (JP); National Institute of Technology and Evaluation, Tokyo (JP); National Research Institute of Brewing, Higashihiroshima-shi (JP)

( * ) Notice: Subject to any disclaimer, the term of this patent is extended or adjusted under 35 U.S.C. 154(b) by 318 days.

(21) Appl. No.: 10/498,517

(22) PCT Filed: Dec. 25, 2002

(86) PCT No.: PCT/JP02/13559

§ 371 (c)(1),
(2), (4) Date: Feb. 22, 2005

(87) PCT Pub. No.: WO03/056016

PCT Pub. Date: Jul. 10, 2003

(65) Prior Publication Data

US 2005/0142650 A1    Jun. 30, 2005

(30) Foreign Application Priority Data

Dec. 27, 2001  (JP) .............................. 2001-403261

(51) Int. Cl.
C12N 9/02   (2006.01)
C12N 15/00  (2006.01)
C12N 1/00   (2006.01)
C12P 21/06  (2006.01)
C07H 21/04  (2006.01)

(52) U.S. Cl. .............. 435/189; 435/320.1; 435/254.11; 435/69.1; 536/23.2

(58) Field of Classification Search ................ 435/189, 435/320.1, 254.1, 69.1; 536/23.2
See application file for complete search history.

(56) References Cited

FOREIGN PATENT DOCUMENTS

| JP | 9-165315 | 6/1997 |
|---|---|---|
| JP | 9-165318 | 6/1997 |
| JP | 2796114 | 6/1998 |
| JP | 2977245 | 9/1999 |
| JP | 2000-327785 | 11/2000 |

OTHER PUBLICATIONS

Tur et al.; "Unprecedented Lysyloxidase Activity of *Pichia pastoris* Benzylamine Oxidase"; FEB 06338; Jul. 8, 1988; vol. 238, No. 1, 74-76.
Kucha et al.; "Cloning, Sequence Analysis, and Characterization of the 'Lysyl Oxidase' from *Pichia pastoris*"; Journal of Inorganic Biochemistry 83 (2001) 193-204.
K. Ja, et al.; "Cloning, sequence analysis, and characterization of the 'lysyl oxidase' from *Pichia pastoris*"; *J. Inorg. Biochem.*; vol. 83(2-3); Jan. 2001; pp. 193-204./Cited in the International Search Report.

*Primary Examiner*—Rebecca E. Prouty
*Assistant Examiner*—Malgorzata A. Walicka
(74) *Attorney, Agent, or Firm*—Edwards Angell Palmer & Dodge LLP

(57) ABSTRACT

Lysyl oxidase derived from filamentous fungi and a DNA encoding thereof are provided. Lysyl oxidase including a protein described in of the following (a) or (b): (a) a protein having an amino acid sequence set forth in SEQ ID NO: 2; or (b) a protein having an amino acid sequence obtained by modifying a part of the amino acid sequence set forth in SEQ ID NO: 2, and functioning as lysyl oxidase.

9 Claims, 5 Drawing Sheets

Fig. 3

```
tgg ctg aac ctg ggg atg cac cac gtc ccg cac acg ggc gac ctg ccg
Trp Leu Asn Leu Gly Met His His Val Pro His Thr Gly Asp Leu Pro>

60
aac acg gtg ttc acg acg gcc cgc tcc ggg gtg cag ttc acg ccg ctg
Asn Thr Val Phe Thr Thr Ala Arg Ser Gly Val Gln Phe Thr Pro Leu>

120
aac tac ctc gcc ggg gac ccg agc cgg cag acg gtg aac atg gtg cga
Asn Tyr Leu Ala Gly Asp Pro Ser Arg Gln Thr Val Asn Met Val Arg>

180
gtg aat tat gcg aat ggg tcg gcg acg gag gtg aag acg ttc ggg cag
Val Asn Tyr Ala Asn Gly Ser Ala Thr Glu Val Lys Thr Phe Gly Gln>

240
gcg gag gag gtc tgt acg gta ccc atc acc ggg atc ggg gag gag cta
Ala Glu Glu Val Cys Thr Val Pro Ile Thr Gly Ile Gly Glu Glu Leu> tgg cgg tat cag ggg gat gta gtg gtg cgg aaa ttc ccg tat aac ccg
Trp Arg Tyr Gln Gly Asp Val Val Val Arg Lys Phe Pro Tyr Asn Pro>

300
aat gat ccg tac tat gag atg gag ggg gat gca tga tgcaca tgtagataga
Asn Asp Pro Tyr Tyr Glu Met Glu Gly Asp Ala ***>

360
tttcctacag gccgaatctg catcggctcc gtgacaaaaa caatttttt aaaagattaa 420
aaaaagataa ccctaatgga gatatttgga aaaataaaaa aaaaaaaaaa aa(a)n
```

Fig. 4
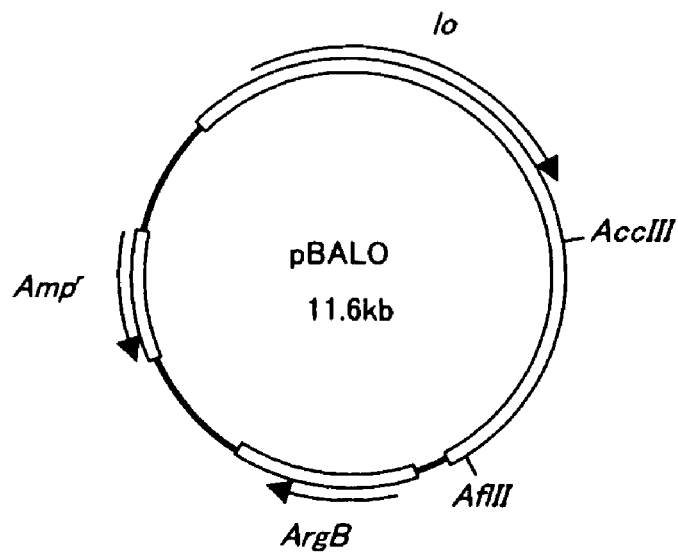
*AccIII, AfIII* digested
9.4kb frag : blanting
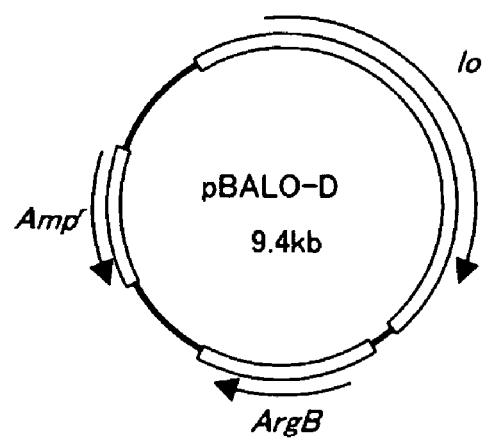

SEQUENCE LISTING

```
<160> NUMBER OF SEQ ID NOS: 24

<210> SEQ ID NO 1
<211> LENGTH: 4650
<212> TYPE: DNA
<213> ORGANISM: Aspergillus oryzae
<220> FEATURE:
<221> NAME/KEY: CDS
<222> LOCATION: (1569)..(1900)
<223> OTHER INFORMATION: synthetic
<220> FEATURE:
<221> NAME/KEY: CDS
<222> LOCATION: (1940)..(3106)
<223> OTHER INFORMATION: synthetic
<220> FEATURE:
<221> NAME/KEY: CDS
<222> LOCATION: (3164)..(4091)
<223> OTHER INFORMATION: synthetic

<400> SEQUENCE: 1
agatctcgct ttttaaagtt cgtacagttc ccactttttc attactcggt caacagcttt      60
gctagcttat actaacccag tgaatcaaac aatcgataat gtattgacag agctgtctgg     120
aaggatggaa ataatataca acaaaagtac cgttctcaac tctcactgct caaagcccgc     180
ccatgtcctc caccttagcg agcacctcgt cacccaaaaa gagcagacca catcctgaaa     240
cgatgccctt caagatcgaa acaactaccc tcctctacta gcgtacatct tctctaacaa     300
ttttctctca tataacctag atcaacaatg gcaggcattc ttcgagtgga agaattcaca     360
cgctatccgc ttaatccgag ataagttccg atactgtggt cttcgaagtc ttcacaatag     420
ggcatagcct tccaaggatt ggaattatag ggataataca taagaattat agctagggta     480
tcagaggagt tacttcgctc cttagagaga gcacttaccc gagccaaata ccaaggatag     540
aaatgattag aagatagact atgttctcgt gcgcttagcc ccttatgatt atgtttctca     600
atttcgcatc atttcagggt attggcgttc ctccagtaaa cgagggtaa actattctgc      660 tagtttgatg gtcgcttata ggctgaagat aaccaacaag aagatacact tcgcttagat     720
cctcgaccat ggtgagcagc cactctgtcc aactttctga aatggcggtg ctaagtatag     780
gaacttgatg atgcaatgac tacaacaagc atcaaaagac cgataaacag cctcggcaaa     840
gcccagcgat caacctctgt ctccaaactg gcatactatg caagtctaac catagtgaaa     900
tactatcaga cgaagtacat catgtatttc atagataaag ctcatgctat ggaacaatta     960
catctcaaca cttctttcat tgaagctgtg acttgatgcc tccgttgctt tgcagcagag    1020
atatgtcccg atacttccgt gacctttgtt tctctttgca tttgtccagg gactgtctcc    1080
```

-continued

```
ccgcagggtc tatcaacgtg ggacgcgata agccccattc ttgacaactg aacggattcg    1140
ctggagataa tcgcaaccgg ttccgatctc atcttcatat acaaagcacg gtcacgctaa    1200
atctctacga ggcccaaccg tatggaaaaa tatcgctacg ggctgaatgt atggggtctt    1260
ggatctatgc taagtcattg tatccagtga gagcatctgc atcattgaca tttccgcctg    1320
taccttctgg tttaggaaaa ttcaacagcg ggctgacgcg atgcacctgg cgggttatgg    1380
tattaggaat cgaagagtga tgaaaatagt tgacaagaca gtctgatatt ggctgagatg    1440
atactcttta ttaaatttta gcttagctag ttccgagcag gccgaatgag acaagtataa    1500
agccatgacc ctggcactta atctcgtccg tctcacaaca gccagtgttt ctgcgtcgt     1560 tggacaac atg agg cta acg atc tcc gcg gca gta ttg cct tcg ttg ctt    1610
         Met Arg Leu Thr Ile Ser Ala Ala Val Leu Pro Ser Leu Leu
         1               5                   10 ctt ctc ccc tgc ttc tta gga gat gct cta gct cat ccg aga cct gat     1658
Leu Leu Pro Cys Phe Leu Gly Asp Ala Leu Ala His Pro Arg Pro Asp
15              20                  25                  30 cct aag aca gca tgg gtg cgt caa ggt cgg aga agg aag agt tcc ccg     1706
Pro Lys Thr Ala Trp Val Arg Gln Gly Arg Arg Arg Lys Ser Ser Pro
                35                  40                  45 cgg aac ctg caa gtc cat tcg tct atg ctc tcg acc tgc gtc gag agc     1754
Arg Asn Leu Gln Val His Ser Ser Met Leu Ser Thr Cys Val Glu Ser
            50                  55                  60 aat gcc act gtg atc aaa gca ccc aag cat aat gtt tgg gaa ggc atg     1802
Asn Ala Thr Val Ile Lys Ala Pro Lys His Asn Val Trp Glu Gly Met
        65                  70                  75 acg gac gag gaa aca gcc tct gtg gtt aag tgg ctc ttc caa caa ccg     1850
Thr Asp Glu Glu Thr Ala Ser Val Val Lys Trp Leu Phe Gln Gln Pro
    80                  85                  90 acg ctg aac ctg act gtc acg gaa ggc gcc gga gag tgg gat aac acg     1898
Thr Leu Asn Leu Thr Val Thr Glu Gly Ala Gly Glu Trp Asp Asn Thr
95                  100                 105                 110 at gtaagcgcca actttcggat cactctcggt ggctaacag g acc agt gcc ctc     1952
Met                                              Thr Ser Ala Leu
                                                             115 gtc gag ctg atg cgc ccc aac aag acg gat gtt tta agc tat ctc gat     2000
Val Glu Leu Met Arg Pro Asn Lys Thr Asp Val Leu Ser Tyr Leu Asp
                120                 125                 130 cac caa ggc cca gca cct agc cgt tac gcg cat gtt gtc ctt gac aac     2048
His Gln Gly Pro Ala Pro Ser Arg Tyr Ala His Val Val Leu Asp Asn
            135                 140                 145 cgc gcc acg act gac cct cat tat gct gat ctt ttg gtc ggg cct cta     2096
Arg Ala Thr Thr Asp Pro His Tyr Ala Asp Leu Leu Val Gly Pro Leu
        150                 155                 160 gcc atc acc aat cag tct acc cct tct tgg acg cca tta gag tat cct     2144
Ala Ile Thr Asn Gln Ser Thr Pro Ser Trp Thr Pro Leu Glu Tyr Pro
    165                 170                 175 tac acg cgc aag act cac ggt cga gtg cgc aat ctc gac gct gac tat     2192
Tyr Thr Arg Lys Thr His Gly Arg Val Arg Asn Leu Asp Ala Asp Tyr
180                 185                 190                 195 agc acc atc tac tct gag tgg ctg tat aag att agc gca tcc att gca     2240
Ser Thr Ile Tyr Ser Glu Trp Leu Tyr Lys Ile Ser Ala Ser Ile Ala
                200                 205                 210 gat atc acc ctg gac ctg ttc aat ggg act gca ttg ggc tta gac aac     2288
Asp Ile Thr Leu Asp Leu Phe Asn Gly Thr Ala Leu Gly Leu Asp Asn
            215                 220                 225 gac act ctt gat ata tgg ggg att gac ccc ctc tgg cag gat gac ggc     2336
Asp Thr Leu Asp Ile Trp Gly Ile Asp Pro Leu Trp Gln Asp Asp Gly
        230                 235                 240
```

```
cgg atc atc cgc tgg gac aca ttc tgg aac atg cca acg gat gag ttc      2384
Arg Ile Ile Arg Trp Asp Thr Phe Trp Asn Met Pro Thr Asp Glu Phe
    245                 250                 255 gac acc ggc agc atc cta ccg ctg gga cta ttc ttc aaa tcc gac gtg      2432
Asp Thr Gly Ser Ile Leu Pro Leu Gly Leu Phe Phe Lys Ser Asp Val
260                 265                 270                 275 act ggg cgt gat cct tct cag tgg aag ctt gaa ggc tgg ctt tac aac      2480
Thr Gly Arg Asp Pro Ser Gln Trp Lys Leu Glu Gly Trp Leu Tyr Asn
                280                 285                 290 gac atc ttc tat gaa acg aca gag gct ttt cgc cat gca ttc ttc tcg      2528
Asp Ile Phe Tyr Glu Thr Thr Glu Ala Phe Arg His Ala Phe Phe Ser
            295                 300                 305 acc gga ttt gtc aag cta aag ccc aac acc gag gga cca tgg gcg cag      2576
Thr Gly Phe Val Lys Leu Lys Pro Asn Thr Glu Gly Pro Trp Ala Gln
        310                 315                 320 acg gac caa cgg ggc cct ata ctt cca caa gac aag cag caa tcg cct      2624
Thr Asp Gln Arg Gly Pro Ile Leu Pro Gln Asp Lys Gln Gln Ser Pro
325                 330                 335 ctc atg gta gcg ccg tca gga gca cgg tac tct gtg gac ctc gac cgc      2672
Leu Met Val Ala Pro Ser Gly Ala Arg Tyr Ser Val Asp Leu Asp Arg
340                 345                 350                 355 aaa tac gtg aca tgg atg gac ttc tcg ttt tac atc agc ttc tct cgt      2720
Lys Tyr Val Thr Trp Met Asp Phe Ser Phe Tyr Ile Ser Phe Ser Arg
                360                 365                 370 gat acc ggc gta tca gtg ttt gat atc cgc tat aaa ggt cag cgc gtg      2768
Asp Thr Gly Val Ser Val Phe Asp Ile Arg Tyr Lys Gly Gln Arg Val
            375                 380                 385 ctg tac gag ttg ggt cta caa gag gca ctc gcc cac tat gcg ggc aac      2816
Leu Tyr Glu Leu Gly Leu Gln Glu Ala Leu Ala His Tyr Ala Gly Asn
        390                 395                 400 gat cca atc caa tcc agc gtc gca tat ctg gac tca tac tac ggc ttt      2864
Asp Pro Ile Gln Ser Ser Val Ala Tyr Leu Asp Ser Tyr Tyr Gly Phe
405                 410                 415 gga ccg tac gcc ttt gag cta gtc aaa ggc tac gac tgt ccg gtc tat      2912
Gly Pro Tyr Ala Phe Glu Leu Val Lys Gly Tyr Asp Cys Pro Val Tyr
420                 425                 430                 435 gca acc tac ctc aac agc tcc ttc tac gtt tcc gag aca aca cac acg      2960
Ala Thr Tyr Leu Asn Ser Ser Phe Tyr Val Ser Glu Thr Thr His Thr
                440                 445                 450 cac att gac agt ctc tgt gtg ttt gag tac gat gcc gac tat cct att      3008
His Ile Asp Ser Leu Cys Val Phe Glu Tyr Asp Ala Asp Tyr Pro Ile
            455                 460                 465 cag cgc cac agc acg tcc gac tac gtc agc agt acg aag aac gta tac      3056
Gln Arg His Ser Thr Ser Asp Tyr Val Ser Ser Thr Lys Asn Val Tyr
        470                 475                 480 ctc acc ctc cga tcc gtg tcc acg atc ggc aac tac gac tat atg acc      3104
Leu Thr Leu Arg Ser Val Ser Thr Ile Gly Asn Tyr Asp Tyr Met Thr
485                 490                 495 agg tgagttcca cgccccgaaa gacgcatgaa atcacacccc attaaccatg            3156
Ser
500 cttccag c tac acg ttc cac atg gat ggc acg att ggc gtc gaa gtc cgc   3206
          Tyr Thr Phe His Met Asp Gly Thr Ile Gly Val Glu Val Arg
                              505                 510 gcc tcc ggc tac atc caa gcc gcc tac tac gcg cac aac gaa gac ttc      3254
Ala Ser Gly Tyr Ile Gln Ala Ala Tyr Tyr Ala His Asn Glu Asp Phe
515                 520                 525                 530 ggc tac cgc atc cac gat gcg ttg tcc ggc agc atg cac gac cac gtc      3302
Gly Tyr Arg Ile His Asp Ala Leu Ser Gly Ser Met His Asp His Val
```

-continued

```
                535                 540                 545
ctc aac ttc aag gcc gac ttc gac atc ctc ggc gtg aac aac agc atc      3350
Leu Asn Phe Lys Ala Asp Phe Asp Ile Leu Gly Val Asn Asn Ser Ile
            550                 555                 560 gag ctc act acg gtg gcc ccg gtc acc cgc acc ttc acc tgg tcc ggc      3398
Glu Leu Thr Thr Val Ala Pro Val Thr Arg Thr Phe Thr Trp Ser Gly
        565                 570                 575 ggc cgc tcg cgc aac acc atg acc ctg gaa cgg tcc atc cta tcg tcc      3446
Gly Arg Ser Arg Asn Thr Met Thr Leu Glu Arg Ser Ile Leu Ser Ser
580                 585                 590 gaa gac gaa ggc cgc ttc aac tgg ggc ccc aac ggg gcg acg atg atg      3494
Glu Asp Glu Gly Arg Phe Asn Trp Gly Pro Asn Gly Ala Thr Met Met
595                 600                 605                 610 cac gtc atc aac cag gac gcc cgc aac ccg tac ggc gag tac cgg ggc      3542
His Val Ile Asn Gln Asp Ala Arg Asn Pro Tyr Gly Glu Tyr Arg Gly
            615                 620                 625 tac cgc gtg ctg ccg gcg gcc ggg aca gca cac ctg acg gtc cag gac      3590
Tyr Arg Val Leu Pro Ala Ala Gly Thr Ala His Leu Thr Val Gln Asp
        630                 635                 640 tcc agc aac ctg gcg cac gcg gcg cac tgg gcc gag tac gac atc cag      3638
Ser Ser Asn Leu Ala His Ala Ala His Trp Ala Glu Tyr Asp Ile Gln
            645                 650                 655 gtc acg cgg cag cac gac cac gag ccg cgc gcc gcg cac gcc tac aac      3686
Val Thr Arg Gln His Asp His Glu Pro Arg Ala Ala His Ala Tyr Asn
660                 665                 670 agc cag gac atc cac aac ccg ccc gtc aac ttc gcc gag ttc ttc gac      3734
Ser Gln Asp Ile His Asn Pro Pro Val Asn Phe Ala Glu Phe Phe Asp
675                 680                 685                 690 ggc gag ccg ctc aac cag acc gat ctg gtc gtg tgg ctg aac ctg ggg      3782
Gly Glu Pro Leu Asn Gln Thr Asp Leu Val Val Trp Leu Asn Leu Gly
            695                 700                 705 atg cac cac gtc ccg cac acg ggc gac ctg ccg aac acg gtg ttc acg      3830
Met His His Val Pro His Thr Gly Asp Leu Pro Asn Thr Val Phe Thr
            710                 715                 720 acg gcc cgc tcc ggg gtg cag ttc acg ccg ctg aac tac ctc gcc ggg      3878
Thr Ala Arg Ser Gly Val Gln Phe Thr Pro Leu Asn Tyr Leu Ala Gly
            725                 730                 735 gac ccg agc cgg cag acg gtg aac atg gtg cga gtg aat tat gcg aat      3926
Asp Pro Ser Arg Gln Thr Val Asn Met Val Arg Val Asn Tyr Ala Asn
        740                 745                 750 ggg tcg gcg acg gag gtg aag acg ttc ggg cag gcg gag gag gtc tgt      3974
Gly Ser Ala Thr Glu Val Lys Thr Phe Gly Gln Ala Glu Glu Val Cys
755                 760                 765                 770 acg gta ccc atc acc ggg atc ggg gag gag cta tgg cgg tat cag ggg      4022
Thr Val Pro Ile Thr Gly Ile Gly Glu Glu Leu Trp Arg Tyr Gln Gly
            775                 780                 785 gat gta gtg gtg cgg aaa ttc ccg tat aac ccg aat gat ccg tac tat      4070
Asp Val Val Val Arg Lys Phe Pro Tyr Asn Pro Asn Asp Pro Tyr Tyr
        790                 795                 800 gag atg gag ggg gat gca tgatgcacat gtagatagat ttcctacagg             4118
Glu Met Glu Gly Asp Ala
            805 ccgaatctgc atcggctccg tgacaaaaac aattttttta aaagattaaa aaaagataac    4178 cctaatggag atatttggaa aaataaaaaa taaaaataca agagaagact atataaaga     4238 ctaataataa aatagagtag cagaatacct attctaagtc acgttatcta ggggtcaggt    4298 gacacaaaag cctttgcggg attcatcccg cagaccctag aacctactaa gtagcgcact    4358 agacagccta agatcaccgc gtgtgcctta cacctataaa tactaaaaat cttaaaaata    4418
```

```
ataaactcta aaatagtgaa atatctatgt agtaaaatta acaattaacc agagaataga    4478
ataataacta aagtataata gaagtggaat atatatataa tagacaagtt ccgatgccga    4538
attgatagct cttgagagaa taatcgaaat ggagatagaa agaagtaagc ctagggtgtg    4598
taataccagt ggcgtattgg tcaatatctg ataattattg actgagtccg ga            4650
```

<210> SEQ ID NO 2
<211> LENGTH: 808
<212> TYPE: PRT
<213> ORGANISM: Aspergillus oryzae

<400> SEQUENCE: 2

```
Met Arg Leu Thr Ile Ser Ala Ala Val Leu Pro Ser Leu Leu Leu Leu
1               5                   10                  15

Pro Cys Phe Leu Gly Asp Ala Leu Ala His Pro Arg Pro Asp Pro Lys
            20                  25                  30

Thr Ala Trp Val Arg Gln Gly Arg Arg Lys Ser Ser Pro Arg Asn
        35                  40                  45

Leu Gln Val His Ser Ser Met Leu Ser Thr Cys Val Glu Ser Asn Ala
    50                  55                  60

Thr Val Ile Lys Ala Pro Lys His Asn Val Trp Glu Gly Met Thr Asp
65                  70                  75                  80

Glu Glu Thr Ala Ser Val Val Lys Trp Leu Phe Gln Gln Pro Thr Leu
                85                  90                  95

Asn Leu Thr Val Thr Glu Gly Ala Gly Glu Trp Asp Asn Thr Met Thr
            100                 105                 110

Ser Ala Leu Val Glu Leu Met Arg Pro Asn Lys Thr Asp Val Leu Ser
        115                 120                 125

Tyr Leu Asp His Gln Gly Pro Ala Pro Ser Arg Tyr Ala His Val Val
    130                 135                 140

Leu Asp Asn Arg Ala Thr Thr Asp Pro His Tyr Ala Asp Leu Leu Val
145                 150                 155                 160

Gly Pro Leu Ala Ile Thr Asn Gln Ser Thr Pro Ser Trp Thr Pro Leu
                165                 170                 175

Glu Tyr Pro Tyr Thr Arg Lys Thr His Gly Arg Val Arg Asn Leu Asp
            180                 185                 190

Ala Asp Tyr Ser Thr Ile Tyr Ser Glu Trp Leu Tyr Lys Ile Ser Ala
        195                 200                 205

Ser Ile Ala Asp Ile Thr Leu Asp Leu Phe Asn Gly Thr Ala Leu Gly
    210                 215                 220

Leu Asp Asn Asp Thr Leu Asp Ile Trp Gly Ile Asp Pro Leu Trp Gln
225                 230                 235                 240

Asp Asp Gly Arg Ile Ile Arg Trp Asp Thr Phe Trp Asn Met Pro Thr
                245                 250                 255

Asp Glu Phe Asp Thr Gly Ser Ile Leu Pro Leu Gly Leu Phe Phe Lys
            260                 265                 270

Ser Asp Val Thr Gly Arg Asp Pro Ser Gln Trp Lys Leu Glu Gly Trp
        275                 280                 285

Leu Tyr Asn Asp Ile Phe Tyr Glu Thr Thr Glu Ala Phe Arg His Ala
    290                 295                 300

Phe Phe Ser Thr Gly Phe Val Lys Leu Lys Pro Asn Thr Glu Gly Pro
305                 310                 315                 320

Trp Ala Gln Thr Asp Gln Arg Gly Pro Ile Leu Pro Gln Asp Lys Gln
                325                 330                 335
```

-continued

```
Gln Ser Pro Leu Met Val Ala Pro Ser Gly Ala Arg Tyr Ser Val Asp
            340                 345                 350
Leu Asp Arg Lys Tyr Val Thr Trp Met Asp Phe Ser Phe Tyr Ile Ser
        355                 360                 365
Phe Ser Arg Asp Thr Gly Val Ser Val Phe Asp Ile Arg Tyr Lys Gly
    370                 375                 380
Gln Arg Val Leu Tyr Glu Leu Gly Leu Gln Glu Ala Leu Ala His Tyr
385                 390                 395                 400
Ala Gly Asn Asp Pro Ile Gln Ser Ser Val Ala Tyr Leu Asp Ser Tyr
                405                 410                 415
Tyr Gly Phe Gly Pro Tyr Ala Phe Glu Leu Val Lys Gly Tyr Asp Cys
            420                 425                 430
Pro Val Tyr Ala Thr Tyr Leu Asn Ser Ser Phe Tyr Val Ser Glu Thr
        435                 440                 445
Thr His Thr His Ile Asp Ser Leu Cys Val Phe Glu Tyr Asp Ala Asp
    450                 455                 460
Tyr Pro Ile Gln Arg His Ser Thr Ser Asp Tyr Val Ser Ser Thr Lys
465                 470                 475                 480
Asn Val Tyr Leu Thr Leu Arg Ser Val Ser Thr Ile Gly Asn Tyr Asp
                485                 490                 495
Tyr Met Thr Ser Tyr Thr Phe His Met Asp Gly Thr Ile Gly Val Glu
            500                 505                 510
Val Arg Ala Ser Gly Tyr Ile Gln Ala Ala Tyr Tyr Ala His Asn Glu
        515                 520                 525
Asp Phe Gly Tyr Arg Ile His Asp Ala Leu Ser Gly Ser Met His Asp
    530                 535                 540
His Val Leu Asn Phe Lys Ala Asp Phe Asp Ile Leu Gly Val Asn Asn
545                 550                 555                 560
Ser Ile Glu Leu Thr Thr Val Ala Pro Val Thr Arg Thr Phe Thr Trp
                565                 570                 575
Ser Gly Gly Arg Ser Arg Asn Thr Met Thr Leu Glu Arg Ser Ile Leu
            580                 585                 590
Ser Ser Glu Asp Glu Gly Arg Phe Asn Trp Gly Pro Asn Gly Ala Thr
        595                 600                 605
Met Met His Val Ile Asn Gln Asp Ala Arg Asn Pro Tyr Gly Glu Tyr
    610                 615                 620
Arg Gly Tyr Arg Val Leu Pro Ala Ala Gly Thr Ala His Leu Thr Val
625                 630                 635                 640
Gln Asp Ser Ser Asn Leu Ala His Ala Ala His Trp Ala Glu Tyr Asp
                645                 650                 655
Ile Gln Val Thr Arg Gln His Asp His Glu Pro Arg Ala Ala His Ala
            660                 665                 670
Tyr Asn Ser Gln Asp Ile His Asn Pro Pro Val Asn Phe Ala Glu Phe
        675                 680                 685
Phe Asp Gly Glu Pro Leu Asn Gln Thr Asp Leu Val Val Trp Leu Asn
    690                 695                 700
Leu Gly Met His His Val Pro His Thr Gly Asp Leu Pro Asn Thr Val
705                 710                 715                 720
Phe Thr Thr Ala Arg Ser Gly Val Gln Phe Thr Pro Leu Asn Tyr Leu
                725                 730                 735
Ala Gly Asp Pro Ser Arg Gln Thr Val Asn Met Val Arg Val Asn Tyr
            740                 745                 750
```

```
Ala Asn Gly Ser Ala Thr Glu Val Lys Thr Phe Gly Gln Ala Glu Glu
        755                 760                 765

Val Cys Thr Val Pro Ile Thr Gly Ile Gly Glu Glu Leu Trp Arg Tyr
        770                 775                 780

Gln Gly Asp Val Val Arg Lys Phe Pro Tyr Asn Pro Asn Asp Pro
785                 790                 795                 800

Tyr Tyr Glu Met Glu Gly Asp Ala
            805

<210> SEQ ID NO 3
<211> LENGTH: 2523
<212> TYPE: DNA
<213> ORGANISM: Aspergillus oryzae

<400> SEQUENCE: 3
atgaggctaa cgatctccgc ggcagtattg ccttcgttgc ttcttctccc ctgcttctta      60
ggagatgctc tagctcatcc gagacctgat cctaagacag catgggtgcg tcaaggtcgg     120
agaaggaaga gttccccgcg gaacctgcaa gtccattcgt ctatgctctc gacctgcgtc     180
gagagcaatg ccactgtgat caaagcaccc aagcataatg tttgggaagg catgacggac     240
gaggaaacag cctctgtggt taagtggctc ttccaacaac cgacgctgaa cctgactgtc     300
acggaaggcg ccggagagtg ggataacacg atgtaagcgc caactttcgg atcactctcg     360
gtggctaaca ggaccagtgc cctcgtcgag ctgatgcgcc caacaagacg gatgttttta     420
agctatctcg atcaccaagg cccagcacct agccgttacg cgcatgttgt ccttgacaac     480
cgcgccacga ctgaccctca ttatgctgat cttttggtcg ggcctctagc catcaccaat     540
cagtctaccc cttcttggac gccattagag tatccttaca cgcgcaagac tcacggtcga     600
gtgcgcaatc tcgacgctga ctatagcacc atctactctg agtggctgta taagattagc     660
gcatccattg cagatatcac cctggacctg ttcaatggga ctgcattggg cttagacaac     720
gacactcttg atatatgggg gattgacccc ctctggcagg atgacggccg gatcatccgc     780
tgggacacat tctggaacat gccaacggat gagttcgaca ccggcagcat cctaccgctg     840
ggactattct tcaaatccga cgtgactggg cgtgatcctt tcagtggaa gcttgaaggc     900 tggctttaca cgacatcttt ctatgaaacg acagaggctt ttcgccatgc attcttctcg     960
accggatttg tcaagctaaa gcccaacacc gagggaccat gggcgcagac ggaccaacgg    1020
ggccctatac ttccacaaga caagcagcaa tcgcctctca tggtagcgcc gtcaggagca    1080
cggtactctg tggacctcga ccgcaaatac gtgacatgga tggacttctc gttttacatc    1140
agcttctctc gtgataccgg cgtatcagtg tttgatatcc gctataaagg tcagcgcgtg    1200
ctgtacgagt tgggtctaca agaggcactc gcccactatg cgggcaacga tccaatccaa    1260
tccagcgtcg catatctgga ctcatactac ggctttggac cgtacgcctt tgagctagtc    1320
aaaggctacg actgtccggt ctatgcaacc tacctcaaca gctccttcta cgtttccgag    1380
acaacacaca cgcacattga cagtctctgt gtgtttgagt acgatgccga ctatcctatt    1440
cagcgccaca gcacgtccga ctacgtcagc agtacgaaga cgtatacct cacccctccga    1500 tccgtgtcca cgatcggcaa ctacgactat atgaccaggt gagttccacg cccgaaaga    1560 cgcatgaaat cacacccccat taaccatgct tccagctaca cgttccacat ggatggcacg    1620
attggcgtcg aagtccgcgc ctccggctac atccaagccg cctactacgc gcacaacgaa    1680
gacttcggct accgcatcca cgatgcgttg tccggcagca tgcacgacca cgtcctcaac    1740
ttcaaggccg acttcgacat cctcggcgtg aacaacagca tcgagctcac tacggtggcc    1800
```

```
ccggtcaccc gcaccttcac ctggtccggc ggccgctcgc gcaacaccat gaccctggaa    1860
cggtccatcc tatcgtccga agacgaaggc cgcttcaact ggggccccaa cggggcgacg    1920
atgatgcacg tcatcaacca ggacgcccgc aacccgtacg gcgagtaccg gggctaccgc    1980
gtgctgccgg cggccgggac agcacacctg acggtccagg actccagcaa cctggcgcac    2040
gcggcgcact gggccgagta cgacatccag gtcacgcggc agcacgacca cgagccgcgc    2100
gccgcgcacg cctacaacag ccaggacatc cacaacccgc ccgtcaactt cgccgagttc    2160
ttcgacggcg agccgctcaa ccagaccgat ctggtcgtgt ggctgaacct ggggatgcac    2220
cacgtcccgc acacgggcga cctgccgaac acggtgttca cgacggcccg ctccggggtg    2280
cagttcacgc cgctgaacta cctcgccggg gacccgagcc ggcagacggt gaacatggtg    2340
cgagtgaatt atgcgaatgg gtcggcgacg gaggtgaaga cgttcgggca ggcggaggag    2400
gtctgtacgg tacccatcac cgggatcggg gaggagctat ggcggtatca gggggatgta    2460
gtggtgcgga aattcccgta taacccgaat gatccgtact atgagatgga gggggatgca    2520
tga                                                                  2523

<210> SEQ ID NO 4
<211> LENGTH: 2427
<212> TYPE: DNA
<213> ORGANISM: Aspergillus oryzae

<400> SEQUENCE: 4
atgaggctaa cgatctccgc ggcagtattg ccttcgttgc ttcttctccc ctgcttctta      60
ggagatgctc tagctcatcc gagacctgat cctaagacag catgggtgcg tcaaggtcgg     120
agaaggaaga gttccccgcg gaacctgcaa gtccattcgt ctatgctctc gacctgcgtc     180
gagagcaatg ccactgtgat caaagcaccc aagcataatg tttgggaagg catgacggac     240
gaggaaacag cctctgtggt taagtggctc ttccaacaac cgacgctgaa cctgactgtc     300
acggaaggcg ccggagagtg ggataacacg atgaccagtg ccctcgtcga gctgatgcgc     360
cccaacaaga cggatgtttt aagctatctc gatcaccaag gcccagcacc tagccgttac     420
gcgcatgttg tccttgacaa ccgcgccacg actgaccctc attatgctga tcttttggtc     480
gggcctctag ccatcaccaa tcagtctacc ccttcttgga cgccattaga gtatccttac     540
acgcgcaaga ctcacggtcg agtgcgcaat ctcgacgctg actatagcac catctactct     600
gagtggctgt ataagattag cgcatccatt gcagatatca ccctggacct gttcaatggg     660
actgcattgg gcttagacaa cgacactctt gatatatggg ggattgaccc cctctggcag     720
gatgacggcc ggatcatccg ctgggacaca ttctggaaca tgccaacgga tgagttcgac     780
accggcagca tcctaccgct gggactattc ttcaaatccg acgtgactgg gcgtgatcct     840
tctcagtgga agcttgaagg ctggctttac aacgacatct tctatgaaac gacagaggct     900
tttcgccatg cattcttctc gaccggattt gtcaagctaa agcccaacac cgagggacca     960
tgggcgcaga cggaccaacg gggccctata cttccacaag acaagcagca atcgcctctc    1020
atggtagcgc cgtcaggagc acggtactct gtggacctcg accgcaaata cgtgacatgg    1080
atggacttct cgttttacat cagcttctct cgtgataccg cgtatcagt gtttgatatc     1140 cgctataaag gtcagcgcgt gctgtacgag ttgggtctac aagaggcact cgcccactat    1200
gcgggcaacg atccaatcca atccagcgtc gcatatctgg actcatacta cggctttgga    1260
ccgtacgcct ttgagctagt caaaggctac gactgtccgg tctatgcaac ctacctcaac    1320
```

-continued

```
agctccttct acgtttccga gacaacacac acgcacattg acagtctctg tgtgtttgag   1380
tacgatgccg actatcctat tcagcgccac agcacgtccg actacgtcag cagtacgaag   1440
aacgtatacc tcaccctccg atccgtgtcc acgatcggca actacgacta tatgaccagc   1500
tacacgttcc acatggatgg cacgattggc gtcgaagtcc gcgcctccgg ctacatccaa   1560
gccgcctact acgcgcacaa cgaagacttc ggctaccgca tccacgatgc gttgtccggc   1620
agcatgcacg accacgtcct caacttcaag gccgacttcg acatcctcgg cgtgaacaac   1680
agcatcgagc tcactacggt ggccccggtc acccgcacct tcacctggtc cggcggccgc   1740
tcgcgcaaca ccatgaccct ggaacggtcc atcctatcgt ccgaagacga aggccgcttc   1800
aactggggcc caacggggc gacgatgatg cacgtcatca accaggacgc ccgcaacccg   1860
tacggcgagt accggggcta ccgcgtgctg ccggcggccg ggacagcaca cctgacggtc   1920
caggactcca gcaacctggc gcacgcggcg cactgggccg agtacgacat ccaggtcacg   1980
cggcagcacg accacgagcc gcgcgccgcg cacgcctaca acagccagga catccacaac   2040
ccgcccgtca acttcgccga gttcttcgac ggcgagccgc tcaaccagac cgatctggtc   2100
gtgtggctga acctggggat gcaccacgtc ccgcacacgg cgacctgcc gaacacggtg   2160 ttcacgacgg cccgctccgg ggtgcagttc acgccgctga actacctcgc cggggacccg   2220
agccggcaga cggtgaacat ggtgcgagtg aattatgcga atgggtcggc gacggaggtg   2280
aagacgttcg ggcaggcgga ggaggtctgt acggtaccca tcaccgggat cggggaggag   2340
ctatggcggt atcaggggga tgtagtggtg cggaaattcc cgtataaccc gaatgatccg   2400
tactatgaga tggaggggga tgcatga                                        2427
```

<210> SEQ ID NO 5
<211> LENGTH: 4091
<212> TYPE: DNA
<213> ORGANISM: Aspergillus oryzae

<400> SEQUENCE: 5

```
agatctcgct ttttaaagtt cgtacagttc ccacttttc attactcggt caacagcttt     60
gctagcttat actaacccag tgaatcaaac aatcgataat gtattgacag agctgtctgg   120
aaggatggaa ataatataca acaaaagtac cgttctcaac tctcactgct caaagcccgc   180
ccatgtcctc caccttagcg agcacctcgt cacccaaaaa gagcagacca catcctgaaa   240
cgatgccctt caagatcgaa acaactaccc tcctctacta gcgtacatct tctctaacaa   300
ttttctctca tataacctag atcaacaatg gcaggcattc ttcgagtgga agaattcaca   360
cgctatccgc ttaatccgag ataagttccg atactgtggt cttcgaagtc ttcacaatag   420
ggcatagcct tccaaggatt ggaattatag ggataataca taagaattat agctagggta   480
tcagaggagt tacttcgctc cttagagaga gcacttaccc gagccaaata ccaaggatag   540
aaatgattag aagatagact atgttctcgt gcgcttagcc ccttatgatt atgtttctca   600
atttcgcatc atttcagggt attggcgttc ctccagtaaa cgaggggtaa actattctgc   660
tagtttgatg gtcgcttata ggctgaagat aaccaacaag aagatacact tcgcttagat   720
cctcgaccat ggtgagcagc cactctgtcc aactttctga atggcggtg ctaagtatag   780 gaacttgatg atgcaatgac tacaacaagc atcaaaagac cgataaacag cctcggcaaa   840
gcccagcgat caacctctgt ctccaaactg gcatactatg caagtctaac catagtgaaa   900
tactatcaga cgaagtacat catgtatttc atagataaag ctcatgctat ggaacaatta   960
catctcaaca cttctttcat tgaagctgtg acttgatgcc tccgttgctt tgcagcagag  1020
```

```
atatgtcccg atacttccgt gacctttgtt tctctttgca tttgtccagg gactgtctcc   1080
ccgcagggtc tatcaacgtg ggacgcgata agccccattc ttgacaactg aacggattcg   1140
ctggagataa tcgcaaccgg ttccgatctc atcttcatat acaaagcacg gtcacgctaa   1200
atctctacga ggcccaaccg tatggaaaaa tatcgctacg ggctgaatgt atgggggtctt  1260 ggatctatgc taagtcattg tatccagtga gagcatctgc atcattgaca tttccgcctg   1320
taccttctgg tttaggaaaa ttcaacagcg ggctgacgcg atgcacctgg cgggttatgg   1380
tattaggaat cgaagagtga tgaaaatagt tgacaagaca gtctgatatt ggctgagatg   1440
atactcttta ttaaatttta gcttagctag ttccgagcag gccgaatgag acaagtataa   1500
agccatgacc ctggcactta atctcgtccg tctcacaaca gccagtgttt tctgcgtcgt   1560
tggacaacat gaggctaacg atctccgcgg cagtattgcc ttcgttgctt cttctcccct   1620
gcttcttagg agatgctcta gctcatccga gacctgatcc taagacagca tgggtgcgtc   1680
aaggtcggag aaggaagagt tccccgcgga acctgcaagt ccattcgtct atgctctcga   1740
cctgcgtcga gagcaatgcc actgtgatca aagcacccaa gcataatgtt tgggaaggca   1800
tgacggacga ggaaacagcc tctgtggtta agtggctctt ccaacaaccg acgctgaacc   1860
tgactgtcac ggaaggcgcc ggagagtggg ataacacgat gtaagcgcca actttcggat   1920
cactctcggt ggctaacagg accagtgccc tcgtcgagct gatgcgcccc aacaagacgg   1980
atgttttaag ctatctcgat caccaaggcc cagcacctag ccgttacgcg catgttgtcc   2040
ttgacaaccg cgccacgact gaccctcatt atgctgatct tttggtcggg cctctagcca   2100
tcaccaatca gtctacccct tcttggacgc cattagagta tccttacacg cgcaagactc   2160
acggtcgagt gcgcaatctc gacgctgact atagcaccat ctactctgag tggctgtata   2220
agattagcgc atccattgca gatatcaccc tggacctgtt caatgggact gcattgggct   2280
tagacaacga cactcttgat atatggggga ttgaccccct ctggcaggat gacggccgga   2340
tcatccgctg ggacacattc tggaacatgc caacggatga gttcgacacc ggcagcatcc   2400
taccgctggg actattcttc aaatccgacg tgactgggcg tgatccttct cagtggaagc   2460
ttgaaggctg gctttacaac gacatcttct atgaaacgac agaggctttt cgccatgcat   2520
tcttctcgac cggatttgtc aagctaaagc ccaacaccga gggaccatgg gcgcagacgg   2580
accaacgggg ccctatactt ccacaagaca agcagcaatc gcctctcatg gtagcgccgt   2640
caggagcacg gtactctgtg gacctcgacc gcaaatacgt gacatggatg gacttctcgt   2700
tttacatcag cttctctcgt gataccggcg tatcagtgtt tgatatccgc tataaaggtc   2760
agcgcgtgct gtacgagttg ggtctacaag aggcactcgc ccactatgcg ggcaacgatc   2820
caatccaatc cagcgtcgca tatctggact catactacgg ctttggaccg tacgcctttg   2880
agctagtcaa aggctacgac tgtccggtct atgcaaccta cctcaacagc tccttctacg   2940
tttccgagac aacacacacg cacattgaca gtctctgtgt gtttgagtac gatgccgact   3000
atcctattca gcgccacagc acgtccgact acgtcagcag tacgaagaac gtatacctca   3060
ccctccgatc cgtgtccacg atcggcaact acgactatat gaccaggtga gttccacgcc   3120
ccgaaagacg catgaaatca caccccatta accatgcttc cagctacacg ttccacatgg   3180
atggcacgat tggcgtcgaa gtccgcgcct ccggctacat ccaagccgcc tactacgcgc   3240
acaacgaaga cttcggctac cgcatccacg atgcgttgtc cggcagcatg cacgaccacg   3300
tcctcaactt caaggccgac ttcgacatcc tcggcgtgaa caacagcatc gagctcacta   3360
```

-continued

```
cggtggcccc ggtcacccgc accttcacct ggtccggcgg ccgctcgcgc aacaccatga   3420
ccctggaacg gtccatccta tcgtccgaag acgaaggccg cttcaactgg ggccccaacg   3480
gggcgacgat gatgcacgtc atcaaccagg acgcccgcaa cccgtacggc gagtaccggg   3540
gctaccgcgt gctgccggcg gccgggacag cacacctgac ggtccaggac tccagcaacc   3600
tggcgcacgc ggcgcactgg gccgagtacg acatccaggt cacgcggcag cacgaccacg   3660
agccgcgcgc cgcgcacgcc tacaacagcc aggacatcca caacccgccc gtcaacttcg   3720
ccgagttctt cgacggcgag ccgctcaacc agaccgatct ggtcgtgtgg ctgaacctgg   3780
ggatgcacca cgtcccgcac acgggcgacc tgccgaacac ggtgttcacg acggcccgct   3840
ccggggtgca gttcacgccg ctgaactacc tcgccgggga cccgagccgg cagacggtga   3900
acatggtgcg agtgaattat gcaatgggtc ggcgacgga ggtgaagacg ttcgggcagg   3960
cggaggaggt ctgtacggta cccatcaccg ggatcgggga ggagctatgg cggtatcagg   4020
gggatgtagt ggtgcggaaa ttcccgtata acccgaatga tccgtactat gagatggagg   4080
gggatgcatg a                                                       4091

<210> SEQ ID NO 6
<211> LENGTH: 3995
<212> TYPE: DNA
<213> ORGANISM: Aspergillus oryzae

<400> SEQUENCE: 6
agatctcgct ttttaaagtt cgtacagttc ccacttttc attactcggt caacagcttt    60
gctagcttat actaacccag tgaatcaaac aatcgataat gtattgacag agctgtctgg   120
aaggatggaa ataatataca acaaaagtac cgttctcaac tctcactgct caaagcccgc   180
ccatgtcctc caccttagcg agcacctcgt cacccaaaaa gagcagacca catcctgaaa   240
cgatgccctt caagatcgaa acaactaccc tcctctacta gcgtacatct tctctaacaa   300
ttttctctca tataacctag atcaacaatg gcaggcattc ttcgagtgga agaattcaca   360
cgctatccgc ttaatccgag ataagttccg atactgtggt cttcgaagtc ttcacaatag   420
ggcatagcct tccaaggatt ggaattatag ggataataca taagaattat agctagggta   480
tcagaggagt tacttcgctc cttagagaga gcacttaccc gagccaaata ccaaggatag   540
aaatgattag aagatagact atgttctcgt gcgcttagcc ccttatgatt atgtttctca   600
atttcgcatc atttcagggt attggcgttc ctccagtaaa cgaggggtaa actattctgc   660
tagtttgatg gtcgcttata ggctgaagat aaccaacaag aagatacact tcgcttagat   720
cctcgaccat ggtgagcagc cactctgtcc aactttctga atggcggtg ctaagtatag   780
gaacttgatg atgcaatgac tacaacaagc atcaaaagac cgataaacag cctcggcaaa   840
gcccagcgat caacctctgt ctccaaactg gcatactatg caagtctaac catagtgaaa   900
tactatcaga cgaagtacat catgtatttc atagataaag ctcatgctat ggaacaatta   960
catctcaaca cttctttcat tgaagctgtg acttgatgcc tccgttgctt gcagcagag   1020
atatgtcccg atacttccgt gacctttgtt tctctttgca tttgtccagg gactgtctcc   1080
ccgcagggtc tatcaacgtg ggacgcgata agcccattc ttgacaactg aacggattcg   1140
ctggagataa tcgcaaccgg ttccgatctc atcttcatat acaaagcacg gtcacgctaa   1200
atctctacga ggcccaaccg tatggaaaaa tatcgctacg ggctgaatgt atggggtctt   1260
ggatctatgc taagtcattg tatccagtga gagcatctgc atcattgaca tttccgcctg   1320
taccttctgg tttaggaaaa ttcaacagcg ggctgacgcg atgcacctgg cgggttatgg   1380
```

```
tattaggaat cgaagagtga tgaaaatagt tgacaagaca gtctgatatt ggctgagatg   1440
atactcttta ttaaatttta gcttagctag ttccgagcag gccgaatgag acaagtataa   1500
agccatgacc ctggcactta atctcgtccg tctcacaaca gccagtgttt tctgcgtcgt   1560
tggacaacat gaggctaacg atctccgcgg cagtattgcc ttcgttgctt cttctcccct   1620
gcttcttagg agatgctcta gctcatccga gacctgatcc taagacagca tgggtgcgtc   1680
aaggtcggag aaggaagagt tccccgcgga acctgcaagt ccattcgtct atgctctcga   1740
cctgcgtcga gagcaatgcc actgtgatca aagcacccaa gcataatgtt tgggaaggca   1800
tgacggacga ggaaacagcc tctgtggtta agtggctctt ccaacaaccg acgctgaacc   1860
tgactgtcac ggaaggcgcc ggagagtggg ataacacgat gaccagtgcc ctcgtcgagc   1920
tgatgcgccc caacaagacg gatgttttaa gctatctcga tcaccaaggc ccagcaccta   1980
gccgttacgc gcatgttgtc cttgacaacc gcgccacgac tgaccctcat tatgctgatc   2040
ttttggtcgg gcctctagcc atcaccaatc agtctacccc ttcttggacg ccattagagt   2100
atccttacac gcgcaagact cacggtcgag tgcgcaatct cgacgctgac tatagcacca   2160
tctactctga gtggctgtat aagattagcg catccattgc agatatcacc ctggacctgt   2220
tcaatgggac tgcattgggc ttagacaacg acactcttga tatatggggg attgacccce   2280 tctggcagga tgacggccgg atcatccgct gggacacatt ctggaacatg ccaacggatg   2340
agttcgacac cggcagcatc ctaccgctgg gactattctt caaatccgac gtgactgggc   2400
gtgatccttc tcagtggaag cttgaaggct ggctttacaa cgacatcttc tatgaaacga   2460
cagaggcttt tcgccatgca ttcttctcga ccggatttgt caagctaaag cccaacaccg   2520
agggaccatg ggcgcagacg gaccaacggg gccctatact tccacaagac aagcagcaat   2580
cgcctctcat ggtagcgccg tcaggagcac ggtactctgt ggacctcgac cgcaaatacg   2640
tgacatggat ggacttctcg ttttacatca gcttctctcg tgataccggc gtatcagtgt   2700
ttgatatccg ctataaaggt cagcgcgtgc tgtacgagtt gggtctacaa gaggcactcg   2760
cccactatgc gggcaacgat ccaatccaat ccagcgtcgc atatctggac tcatactacg   2820
gctttggacc gtacgccttt gagctagtca aaggctacga ctgtccggtc tatgcaacct   2880
acctcaacag ctccttctac gtttccgaga caacacacac gcacattgac agtctctgtg   2940
tgtttgagta cgatgccgac tatcctattc agcgccacag cacgtccgac tacgtcagca   3000
gtacgaagaa cgtatacctc accctccgat ccgtgtccac gatcggcaac tacgactata   3060
tgaccagcta cacgttccac atggatggca cgattggcgt cgaagtccgc gcctccggct   3120
acatccaagc cgcctactac gcgcacaacg aagacttcgg ctaccgcatc cacgatgcgt   3180
tgtccggcag catgcacgac cacgtcctca acttcaaggc cgacttcgac atcctcggcg   3240
tgaacaacag catcgagctc actacggtgg ccccggtcac ccgcaccttc acctggtccg   3300
gcggccgctc gcgcaacacc atgaccctgg aacggtccat cctatcgtcc gaagacgaag   3360
gccgcttcaa ctggggcccc aacggggcga cgatgatgca cgtcatcaac caggacgccc   3420
gcaacccgta cggcgagtac cggggctacc gcgtgctgcc ggcggccggg acagcacacc   3480
tgacggtcca ggactccagc aacctggcgc acgcggcgca ctgggccgag tacgacatcc   3540
aggtcacgcg gcagcacgac cacgagccgc gcgccgcgca cgcctacaac agccaggaca   3600
tccacaaccc gcccgtcaac ttcgccgagt tcttcgacgg cgagccgctc aaccagaccg   3660
atctggtcgt gtggctgaac ctggggatgc accacgtccc gcacacgggc gacctgccga   3720
```

-continued

| | |
|---|---|
| acacggtgtt cacgacggcc cgctccgggg tgcagttcac gccgctgaac tacctcgccg | 3780 |
| gggacccgag ccggcagacg gtgaacatgg tgcgagtgaa ttatgcgaat gggtcggcga | 3840 |
| cggaggtgaa gacgttcggg caggcggagg aggtctgtac ggtacccatc accgggatcg | 3900 |
| gggaggagct atggcggtat caggggggatg tagtggtgcg gaaattcccg tataacccga | 3960 |
| atgatccgta ctatgagatg gaggggatg catga | 3995 |

<210> SEQ ID NO 7
<211> LENGTH: 4554
<212> TYPE: DNA
<213> ORGANISM: Aspergillus oryzae

<400> SEQUENCE: 7

| | |
|---|---|
| agatctcgct ttttaaagtt cgtacagttc ccacttttc attactcggt caacagcttt | 60 |
| gctagcttat actaacccag tgaatcaaac aatcgataat gtattgacag agctgtctgg | 120 |
| aaggatggaa ataatataca acaaaagtac cgttctcaac tctcactgct caaagcccgc | 180 |
| ccatgtcctc caccttagcg agcacctcgt cacccaaaaa gagcagacca catcctgaaa | 240 |
| cgatgccctt caagatcgaa acaactaccc tcctctacta gcgtacatct tctctaacaa | 300 |
| ttttctctca tataacctag atcaacaatg gcaggcattc ttcgagtgga agaattcaca | 360 |
| cgctatccgc ttaatccgag ataagttccg atactgtggt cttcgaagtc ttcacaatag | 420 |
| ggcatagcct tccaaggatt ggaattatag ggataataca taagaattat agctagggta | 480 |
| tcagaggagt tacttcgctc cttagagaga gcacttaccc gagccaaata ccaaggatag | 540 |
| aaatgattag aagatagact atgttctcgt gcgcttagcc ccttatgatt atgtttctca | 600 |
| atttcgcatc atttcagggt attggcgttc ctccagtaaa cgaggggtaa actattctgc | 660 |
| tagtttgatg gtcgcttata ggctgaagat aaccaacaag aagatacact tcgcttagat | 720 |
| cctcgaccat ggtgagcagc cactctgtcc aactttctga aatggcggtg ctaagtatag | 780 |
| gaacttgatg atgcaatgac tacaacaagc atcaaaagac cgataaacag cctcggcaaa | 840 |
| gcccagcgat caacctctgt ctccaaactg gcatactatg caagtctaac catagtgaaa | 900 |
| tactatcaga cgaagtacat catgtatttc atagataaag ctcatgctat ggaacaatta | 960 |
| catctcaaca cttcttttcat tgaagctgtg acttgatgcc tccgttgctt tgcagcagag | 1020 |
| atatgtcccg atacttccgt gacctttgtt tctctttgca tttgtccagg gactgtctcc | 1080 |
| ccgcagggtc tatcaacgtg ggacgcgata agcccattc ttgacaactg aacggattcg | 1140 |
| ctggagataa tcgcaaccgg ttccgatctc atcttcatat acaaagcacg gtcacgctaa | 1200 |
| atctctacga ggcccaaccg tatggaaaaa tatcgctacg ggctgaatgt atggggtctt | 1260 |
| ggatctatgc taagtcattg tatccagtga gagcatctgc atcattgaca tttccgcctg | 1320 |
| taccttctgg tttaggaaaa ttcaacagcg ggctgacgcg atgcacctgg cggggttatgg | 1380 |
| tattaggaat cgaagagtga tgaaaatagt tgacaagaca gtctgatatt ggctgagatg | 1440 |
| atactcttta ttaaatttta gcttagctag ttccgagcag gccgaatgag acaagtataa | 1500 |
| agccatgacc ctggcactta atctcgtccg tctcacaaca gccagtgttt tctgcgtcgt | 1560 |
| tggacaacat gaggctaacg atctccgcgg cagtattgcc ttcgttgctt cttctcccct | 1620 |
| gcttcttagg agatgctcta gctcatccga gacctgatcc taagacagca tgggtgcgtc | 1680 |
| aaggtcggag aaggaagagt tccccgcgga acctgcaagt ccattcgtct atgctctcga | 1740 |
| cctgcgtcga gagcaatgcc actgtgatca aagcacccaa gcataatgtt tgggaaggca | 1800 |
| tgacggacga ggaaacagcc tctgtggtta agtggctctt ccaacaaccg acgctgaacc | 1860 |

```
tgactgtcac ggaaggcgcc ggagagtggg ataacacgat gaccagtgcc ctcgtcgagc    1920
tgatgcgccc caacaagacg gatgttttaa gctatctcga tcaccaaggc ccagcaccta    1980
gccgttacgc gcatgttgtc cttgacaacc gcgccacgac tgaccctcat tatgctgatc    2040
ttttggtcgg gcctctagcc atcaccaatc agtctacccc ttcttggacg ccattagagt    2100
atccttacac gcgcaagact cacggtcgag tgcgcaatct cgacgctgac tatagcacca    2160
tctactctga gtggctgtat aagattagcg catccattgc agatatcacc ctggacctgt    2220
tcaatgggac tgcattgggc ttagacaacg acactcttga tatatggggg attgaccccc    2280
tctggcagga tgacggccgg atcatccgct gggacacatt ctggaacatg ccaacggatg    2340
agttcgacac cggcagcatc ctaccgctgg gactattctt caaatccgac gtgactgggc    2400
gtgatccttc tcagtggaag cttgaaggct ggctttacaa cgacatcttc tatgaaacga    2460
cagaggcttt tcgccatgca ttcttctcga ccggatttgt caagctaaag cccaacaccg    2520
agggaccatg ggcgcagacg gaccaacggg gccctatact tccacaagac aagcagcaat    2580
cgcctctcat ggtagcgccg tcaggagcac ggtactctgt ggacctcgac cgcaaatacg    2640
tgacatggat ggacttctcg ttttacatca gcttctctcg tgataccggc gtatcagtgt    2700
ttgatatccg ctataaaggt cagcgcgtgc tgtacgagtt gggtctacaa gaggcactcg    2760
cccactatgc gggcaacgat ccaatccaat ccagcgtcgc atatctggac tcatactacg    2820
gctttggacc gtacgccttt gagctagtca aaggctacga ctgtccggtc tatgcaacct    2880
acctcaacag ctccttctac gtttccgaga caacacacac gcacattgac agtctctgtg    2940
tgtttgagta cgatgccgac tatcctattc agcgccacag cacgtccgac tacgtcagca    3000
gtacgaagaa cgtataccte accctccgat ccgtgtccac gatcggcaac tacgactata    3060
tgaccagcta cacgttccac atggatggca cgattggcgt cgaagtccgc gcctccggct    3120
acatccaagc cgcctactac gcgcacaacg aagacttcgg ctaccgcatc cacgatgcgt    3180
tgtccggcag catgcacgac cacgtcctca acttcaaggc cgacttcgac atcctcggcg    3240
tgaacaacag catcgagctc actacggtgg ccccggtcac ccgcaccttc acctggtccg    3300
gcggccgctc gcgcaacacc atgaccctgg aacggtccat cctatcgtcc gaagacgaag    3360
gccgcttcaa ctggggcccc aacggggcga cgatgatgca cgtcatcaac caggacgccc    3420
gcaacccgta cggcgagtac cggggctacc gcgtgctgcc ggcggccggg acagcacacc    3480
tgacggtcca ggactccagc aacctggcgc acgcggcgca ctgggccgag tacgacatcc    3540
aggtcacgcg gcagcacgac cacgagccgc gcgccgcgca cgcctacaac agccaggaca    3600
tccacaaccc gcccgtcaac ttcgccgagt tcttcgacgg cgagccgctc aaccagaccg    3660
atctggtcgt gtggctgaac ctggggatgc accacgtccc gcacacgggc gacctgccga    3720
acacggtgtt cacgacggcc cgctccgggg tgcagttcac gccgctgaac tacctcgccg    3780
gggacccgag ccggcagacg gtgaacatgg tgcgagtgaa ttatgcgaat gggtcggcga    3840
cggaggtgaa gacgttcggg caggcggagg aggtctgtac ggtacccatc accgggatcg    3900
gggaggagct atggcggtat caggggggatg tagtggtgcg gaaattcccg tataacccga    3960
atgatccgta ctatgagatg gagggggatg catgatgcac atgtagatag atttcctaca    4020
ggccgaatct gcatcggctc cgtgacaaaa acaatttttt taaaagatta aaaaagata     4080 accctaatgg agatatttgg aaaaataaaa aataaaaata caagagaaga ctatataaaa    4140
gactaataat aaaatagagt agcagaatac ctattctaag tcacgttatc tagggtcag    4200
```

| | |
|---|---|
| gtgacacaaa agcctttgcg ggattcatcc cgcagaccct agaacctact aagtagcgca | 4260 |
| ctagacagcc taagatcacc gcgtgtgcct tacacctata aatactaaaa atcttaaaaa | 4320 |
| taataaactc taaaatagtg aaatatctat gtagtaaaat taacaattaa ccagagaata | 4380 |
| gaataataac taaagtataa tagaagtgga atatatatat aatagacaag ttccgatgcc | 4440 |
| gaattgatag ctcttgagag aataatcgaa atggagatag aaagaagtaa gcctagggtg | 4500 |
| tgtaatacca gtggcgtatt ggtcaatatc tgataattat tgactgagtc cgga | 4554 |

<210> SEQ ID NO 8
<211> LENGTH: 6007
<212> TYPE: DNA
<213> ORGANISM: Aspergillus oryzae

<400> SEQUENCE: 8

| | |
|---|---|
| gtgcgcttag ccccttatga ttatgtttct caatttcgca tcatttcagg gtattggcgt | 60 |
| tcctccagta aacgaggggt aaactattct gctagtttga tggtcgctta taggctgaag | 120 |
| ataaccaaca agaagataca cttcgcttag atcctcgacc atggtgagca gccactctgt | 180 |
| ccaactttct gaaatggcgg tgctaagtat aggaacttga tgatgcaatg actacaacaa | 240 |
| gcatcaaaag accgataaac agcctcggca agcccagcg atcaacctct gtctccaaac | 300 |
| tggcatacta tgcaagtcta accatagtga aatactatca gacgaagtac atcatgtatt | 360 |
| tcatagataa agctcatgct atggaacaat tacatctcaa cacttctttc attgaagctg | 420 |
| tgacttgatg cctccgttgc tttgcagcag agatatgtcc cgatacttcc gtgacctttg | 480 |
| tttctctttg catttgtcca gggactgtct ccccgcaggg tctatcaacg tgggacgcga | 540 |
| taagccccat tcttgacaac tgaacggatt cgctggagat aatcgaaacc ggttccgatc | 600 |
| tcatcttcat atacaaagca cggtcacgct aaatctctac gaggcccaac cgtatggaaa | 660 |
| aatatcgcta cgggctgaat gtatgggtc ttggatctat gctaagtcat tgtatccagt | 720 |
| gagagcatct gcatcattga catttccgcc tgtaccttct ggtttaggaa aattcaacag | 780 |
| cgggctgacg cgatgcacct ggcgggttat ggtattagga atcgaagagt gatgaaaata | 840 |
| gttgacaaga cagtctgata ttggctgaga tgatactctt tattaaatt tagcttagct | 900 |
| agttccgagc aggccgaatg agacaagtat aaagccatga ccctggcact taatctcgtc | 960 |
| cgtctcacaa cagccagtgt tttctgcgtc gttggacaac atgaggctaa cgatctccgc | 1020 |
| ggcagtattg ccttcgttgc ttcttctccc ctgcttctta ggagatgctc tagctcatcc | 1080 |
| gagacctgat cctaagacag catgggtgcg tcaaggtcgg agaaggaaga gttccccgcg | 1140 |
| gaacctgcaa gtccattcgt ctatgctctc gacctgcgtc gagagcaatg ccactgtgat | 1200 |
| caaagcaccc aagcataatg tttgggaagg catgacggac gaggaaacag cctctgtggt | 1260 |
| taagtggctc ttccaacaac cgacgctgaa cctgactgtc acggaaggcg ccggagagtg | 1320 |
| ggataacacg atgtaagcgc caactttcgg atcactctcg gtggctaaca ggaccagtgc | 1380 |
| cctcgtcgag ctgatgcgcc ccaacaagac ggatgtttta agctatctcg atcaccaagg | 1440 |
| cccagcacct agccgttacg cgcatgttgt ccttgacaac cgcgccacga ctgaccctca | 1500 |
| ttatgctgat cttttggtcg ggcctctagc catcaccaat cagtctaccc cttcttggac | 1560 |
| gccattagag tatccttaca cgcgcaagac tcacggtcga gtgcgcaatc tcgacgctga | 1620 |
| ctatagcacc atctactctg agtggctgta taagattagc gcatccattg cagatatcac | 1680 |
| cctggacctg ttcaatggga ctgcattggg cttagacaac gacactcttg atatatgggg | 1740 |
| gattgacccc ctctggcagg atgacggccg gatcatccgc tgggacacat tctggaacat | 1800 |

```
gccaacggat gagttcgaca ccggcagcat cctaccgctg ggactattct tcaaatccga    1860
cgtgactggg cgtgatcctt ctcagtggaa gcttgaaggc tggctttaca acgacatctt    1920
ctatgaaacg acagaggctt ttcgccatgc attcttctcg accggatttg tcaagctaaa    1980
gcccaacacc gagggaccat gggcgcagac ggaccaacgg ggccctatac ttccacaaga    2040
caagcagcaa tcgcctctca tggtagcgcc gtcaggagca cggtactctg tggacctcga    2100
ccgcaaatac gtgacatgga tggacttctc gttttacatc agcttctctc gtgataccgg    2160
cgtatcagtg tttgatatcc gctataaagg tcagcgcgtg ctgtacgagt tgggtctaca    2220
agaggcactc gcccactatg cgggcaacga tccaatccaa tccagcgtcg catatctgga    2280
ctcatactac ggctttggac cgtacgcctt tgagctagtc aaaggctacg actgtccggt    2340
ctatgcaacc tacctcaaca gctccttcta cgtttccgag acaacacaca cgcacattga    2400
cagtctctgt gtgtttgagt acgatgccga ctatcctatt cagcgccaca gcacgtccga    2460
ctacgtcagc agtacgaaga acgtatacct caccctccga tccgtgtcca cgatcggcaa    2520
ctacgactat atgaccaggt gagttccacg ccccgaaaga cgcatgaaat cacaccccat    2580
taaccatgct tccagctaca cgttccacat ggatggcacg attggcgtcg aagtccgcgc    2640
ctccggctac atccaagccg cctactacgc gcacaacgaa gacttcggct accgcatcca    2700
cgatgcgttg tccggcagca tgcacgacca cgtcctcaac ttcaaggccg acttcgacat    2760
cctcggcgtg aacaacagca tcgagctcac tacggtggcc ccggtcaccc gcaccttcac    2820
ctggtccggc ggccgctcgc gcaacaccat gaccctggaa cggtccatcc tatcgtccga    2880
agacgaaggc cgcttcaact ggggcccaa cggggcgacg atgatgcacg tcatcaacca    2940
ggacgcccgc aacccgtacg gcgagtaccg gggctaccgc gtgctgccgg cggccgggac    3000
agcacacctg acggtccagg actccagcaa cctggcgcac gcggcgcact gggccgagta    3060
cgacatccag gtcacgcggc agcacgacca cgagccgcgc gccgcgcacg cctacaacag    3120
ccaggacatc cacaacccgc ccgtcaactt cgccgagttc ttcgacggcg agccgctcaa    3180
ccagaccgat ctggtcgtgt ggctgaacct ggggatgcac cacgtcccgc acacgggcga    3240
cctgccgaac acggtgttca cgacggcccg ctccggggtg cagttcacgc cgctgaacta    3300
cctcgccggg gacccgagcc ggcagacggt gaacatggtg cgagtgaatt atgcgaatgg    3360
gtcggcgacg gaggtgaaga cgttcgggca ggcggaggag gtctgtacgg tacccatcac    3420
cgggatcggg gaggagctat ggcggtatca ggggatgta gtggtgcgga aattcccgta    3480
taacccgaat gatccgtact atgagatgga ggggatgca tgatgcacat gtagatagat    3540
ttcctacagg ccgaatctgc atcggctccg tgacaaaaac aatttttta aaagattaaa    3600 aaaagataac cctaatggag atatttggaa aaataaaaaa taaaaataca agagaagact    3660
atataaaaga ctaataataa aatagagtag cagaatacct attctaagtc acgttatcta    3720
ggggtcaggt gacacaaaag cctttgcggg attcatcccg cagaccctag aacctactaa    3780
gtagcgcact agacagccta agatcaccgc gtgtgcctta cacctataaa tactaaaaat    3840
cttaaaaata ataaactcta aaatagtgaa atatctatgt agtaaaatta acaattaacc    3900
agagaataga ataataacta aagtataata gaagtggaat atatatataa tagcaagtt    3960 ccgatgccga attgatagct cttgagagaa taatcgaaat ggagatagaa agaagtaagc    4020
ctagggtgtg taataccagt ggcgtattgg tcaatatctg ataattattg actgagtccg    4080
gagtgttcgc accagaatcg ggagtcggag tccacccgat gtcacgagaa caggtacaaa    4140
```

```
gaggaaggga ttgccccggt ggaggccaga ttctcaaagc ccattccagc tcaacgggtt    4200
tggtttgttt gcatgcgacc gaccattcta gacacggtcg ccaattcaaa gagcttctgc    4260
tgccaagatt cacctataaa tagaatctgt aatcaagtaa gaattaaaag ttgtatctat    4320
cattatctat ctctatatcg cacttttctt gtaaaaccct tcccgtataa cacatacaaa    4380
gaaaacgtaa atatcagaga cccaggtata ccgtatatat taagccaaga gcgccgtgta    4440
gtggcgctta gtcaatgtac ttgggaagcg tcttcaggat gccgtcccgg gcgatgtcct    4500
ccatcgcttt ggtgatttcc tggaggaacc tcttgtcgcc gcgcaagtcg tcaccgaaca    4560
ggctcttgat gctgaggagc tcggccgggc tggtgcctcc tgcgcgagcc ttggcctgga    4620
gctcctcgcg catcgggtcg tcgacctcga acttcttgcc gctgtcgtcg acgccgttaa    4680
tgtaatggaa ccaggcagcc gcaacgaaac acaggcggcg gaatgggcca gtaacccaga    4740
tcgcctcagc aatcgaaggc atgataaatt gtgggatctt gcccgaagcg ttgaggcaga    4800
tgcggggcag ttggtccatg atggtggggt tggagaagcg ctcgatgagc gtcttgcaat    4860
actcatcaat gttgacgccc gggatctcgg gcaacaacgg cttcacctcg tcctgcatca    4920
tttgccacac aaacttgctg aacagtgggt tctccatcac ctcgtggaca tatttgaagc    4980
cggccagctg ccctgggtag ccgatggccg agtggctgcc gttgagcagg cgcagcttgt    5040
gcttctcgaa ttcctcgacg tcatggacat tcttgaccac ctgggcacca accttctcga    5100
atggtgggcg gccatcggag aactgatcct caattaccca ctgcataaag ggctctgtga    5160
cgacgggcca cgagtcctcg atggcaaagt tgtctgcgag tgccgtttta tcggtggcgg    5220
atgtctgagg ggtgatacgg tcgaccatgg cgttgggaa  ggcgccctgt tcggcaatcc    5280
acttcgcgat ctcggggttg cgcaggcgcg caaaggactc gagcatgtgg cgagtgatgg    5340
aaccgttctt ctgcatgttg tcacacgaca tgacggtaaa gggcttgagc ccttgctggt    5400
agcggcgtgc cagagcggca tagaggaagc gaacgtggt gcgcgggac ttctcgttcg    5460 ctggttggag gtcgaactga atgtcagggt gctcactttg gagctcgtgt gtgttctcgt    5520
tgtagtagta accgctctcg gtgatagtga gcgacacaat gtgggtatcc gggtgcgcca    5580
tcttggcgat gacggcctcg cggttatcgg gggcaaagag ataggaattg atgctcccaa    5640
caacatgggc aaagctgccc ttggccgaac gctcaatgac ggtgtagagg tggtcctgcg    5700
accctaaggc gtcgcgcatg gcggcgtcaa agggctgcaa accaacacca caaatcgcgt    5760
agtcagtcac accatgcttc tgcatcaact ggtcgacata aacggccaag tgagctctgt    5820
ggaagccgcc gacgccgacg tggacaattc cctccttcac gtcgccacca cgcttgtagg    5880 ttgggaccctt gacttgggtc tcacctgccg ccgcaatttg cgacaggttt ttgttgttga    5940
gcttcagggg agccattgtg aatgtgtgaa gagtgagaga gaggaattga aagaaagaca    6000
agggcga                                                              6007
```

<210> SEQ ID NO 9
<211> LENGTH: 453
<212> TYPE: DNA
<213> ORGANISM: Aspergillus oryzae

<400> SEQUENCE: 9

```
tggctgaacc tggggatgca ccacgtcccg cacacgggcg acctgccgaa cacggtgttc      60
acgacggccc gctccggggt gcagttcacg ccgctgaact acctcgccgg ggacccgagc     120
cggcagacgt gaacatggt gcgagtgaat tatgcgaatg gtcggcgac ggaggtgaag       180 acgttcgggc aggcggagga ggtctgtacg gtacccatca ccgggatcgg ggaggagcta     240
```

-continued

```
tggcggtatc aggggatgt agtggtgcgg aaattcccgt ataacccgaa tgatccgtac      300
tatgagatgg aggggatgc atgatgcaca tgtagataga tttcctacag gccgaatctg     360
catcggctcc gtgacaaaaa caatttttt aaaagattaa aaaagataa ccctaatgga      420
gatatttgga aaataaaaa aaaaaaaaa aaa                                    453
```

<210> SEQ ID NO 10
<211> LENGTH: 6960
<212> TYPE: DNA
<213> ORGANISM: Aspergillus oryzae

<400> SEQUENCE: 10

```
agatctcgct ttttaaagtt cgtacagttc ccactttttc attactcggt caacagcttt     60
gctagcttat actaacccag tgaatcaaac aatcgataat gtattgacag agctgtctgg    120
aaggatggaa ataatataca acaaaagtac cgttctcaac tctcactgct caaagcccgc    180
ccatgtcctc caccttagcg agcacctcgt cacccaaaaa gagcagacca catcctgaaa    240
cgatgccctt caagatcgaa acaactaccc tcctctacta gcgtacatct tctctaacaa    300
ttttctctca tataacctag atcaacaatg gcaggcattc ttcgagtgga agaattcaca    360
cgctatccgc ttaatccgag ataagttccg atactgtggt cttcgaagtc ttcacaatag    420
ggcatagcct tccaaggatt ggaattatag ggataataca taagaattat agctagggta    480
tcagaggagt tacttcgctc cttagagaga gcacttaccc gagccaaata ccaaggatag    540
aaatgattag aagatagact atgttctcgt gcgcttagcc ccttatgatt atgtttctca    600
atttcgcatc atttcagggt attggcgttc ctccagtaaa cgaggggtaa actattctgc    660
tagtttgatg gtcgcttata ggctgaagat aaccaacaag aagatacact tcgcttagat    720
cctcgaccat ggtgagcagc cactctgtcc aactttctga atggcggtg ctaagtatag     780
gaacttgatg atgcaatgac tacaacaagc atcaaaagac cgataaacag cctcggcaaa    840
gcccagcgat caacctctgt ctccaaactg gcatactatg caagtctaac catagtgaaa    900
tactatcaga cgaagtacat catgtatttc atagataaag ctcatgctat ggaacaatta    960
catctcaaca cttctttcat tgaagctgtg acttgatgcc tccgttgctt gcagcagag    1020
atatgtcccg atacttccgt gacctttgtt tctctttgca tttgtccagg gactgtctcc    1080
ccgcagggtc tatcaacgtg ggacgcgata agccccattc ttgacaactg aacggattcg    1140
ctggagataa tcgcaaccgg ttccgatctc atcttcatat acaaagcacg gtcacgctaa    1200
atctctacga ggcccaaccg tatggaaaaa tatcgctacg ggctgaatgt atgggtctt    1260
ggatctatgc taagtcattg tatccagtga gagcatctgc atcattgaca tttccgcctg    1320
taccttctgg tttaggaaaa ttcaacagcg ggctgacgcg atgcacctgg cgggttatgg    1380
tattaggaat cgaagagtga tgaaaatagt tgacaagaca gtctgatatt ggctgagatg    1440
atactcttta ttaaatttta gcttagctag ttccgagcag gccgaatgag acaagtataa    1500
agccatgacc ctggcactta atctcgtccg tctcacaaca gccagtgttt tctgcgtcgt    1560
tggacaacat gaggctaacg atctccgcgg cagtattgcc ttcgttgctt cttctcccct    1620
gcttcttagg agatgctcta gctcatccga gacctgatcc taagacagca tgggtgcgtc    1680
aaggtcggag aaggaagagt tccccgcgga acctgcaagt ccattcgtct atgctctcga    1740
cctgcgtcga gagcaatgcc actgtgatca aagcacccaa gcataatgtt tgggaaggca    1800
tgacggacga ggaaacagcc tctgtggtta agtggctctt ccaacaaccg acgctgaacc    1860
```

```
tgactgtcac ggaaggcgcc ggagagtggg ataacacgat gtaagcgcca actttcggat     1920
cactctcggt ggctaacagg accagtgccc tcgtcgagct gatgcgcccc aacaagacgg     1980
atgttttaag ctatctcgat caccaaggcc cagcacctag ccgttacgcg catgttgtcc     2040
ttgacaaccg cgccacgact gaccctcatt atgctgatct tttggtcggg cctctagcca     2100
tcaccaatca gtctaccect tcttggacgc cattagagta tccttacacg cgcaagactc     2160
acggtcgagt gcgcaatctc gacgctgact atagcaccat ctactctgag tggctgtata     2220
agattagcgc atccattgca gatatcaccc tggacctgtt caatgggact gcattgggct     2280
tagacaacga cactcttgat atatggggga ttgacccccct ctggcaggat gacggccgga   2340
tcatccgctg ggacacattc tggaacatgc caacggatga gttcgacacc ggcagcatcc     2400
taccgctggg actattcttc aaatccgacg tgactgggcg tgatccttct cagtggaagc     2460
ttgaaggctg gctttacaac gacatcttct atgaaacgac agaggctttt cgccatgcat     2520
tcttctcgac cggatttgtc aagctaaagc ccaacaccga gggaccatgg gcgcagacgg     2580
accaacgggg ccctatactt ccacaagaca agcagcaatc gcctctcatg gtagcgccgt     2640
caggagcacg gtactctgtg gacctcgacc gcaaatacgt gacatggatg gacttctcgt     2700
tttacatcag cttctctcgt gataccggcg tatcagtgtt tgatatccgc tataaaggtc     2760
agcgcgtgct gtacgagttg ggtctacaag aggcactcgc ccactatgcg ggcaacgatc     2820
caatccaatc cagcgtcgca tatctggact catactacgg ctttggaccg tacgcctttg     2880
agctagtcaa aggctacgac tgtccggtct atgcaaccta cctcaacagc tccttctacg     2940
tttccgagac aacacacacg cacattgaca gtctctgtgt gtttgagtac gatgccgact     3000
atcctattca gcgccacagc acgtccgact acgtcagcag tacgaagaac gtataccttca    3060 ccctccgatc cgtgtccacg atcggcaact acgactatat gaccaggtga gttccacgcc     3120
ccgaaagacg catgaaatca cacccccatta accatgcttc cagctacacg ttccacatgg    3180
atggcacgat tggcgtcgaa gtccgcgcct ccggctacat ccaagccgcc tactacgcgc     3240
acaacgaaga cttcggctac cgcatccacg atgcgttgtc cggcagcatg cacgaccacg     3300
tcctcaactt caaggccgac ttcgacatcc tcggcgtgaa caacagcatc gagctcacta     3360
cggtggcccc ggtcacccgc accttcacct ggtccggcgg ccgctcgcgc aacaccatga     3420
ccctggaacg gtccatccta tcgtccgaag acgaaggccg cttcaactgg ggccccaacg     3480
gggcgacgat gatgcacgtc atcaaccagg acgcccgcaa cccgtacggc gagtaccggg     3540
gctaccgcgt gctgccggcg gccgggacag cacacctgac ggtccaggac tccagcaacc     3600
tggcgcacgc ggcgcactgg gccgagtacg acatccaggt cacgcggcag cacgaccacg     3660
agccgcgcgc cgcgcacgcc tacaacagcc aggacatcca caacccgccc gtcaacttcg     3720
ccgagttctt cgacggcgag ccgctcaacc agaccgatct ggtcgtgtgg ctgaacctgg     3780
ggatgcacca cgtcccgcac acgggcgacc tgccgaacac ggtgttcacg acggcccgct     3840
ccggggtgca gttcacgccg ctgaactacc tcgccgggga cccgagccgg cagacggtga     3900
acatggtgcg agtgaattat gcgaatgggt cggcgacgga ggtgaagacg ttcgggcagg     3960
cggaggaggt ctgtacggta cccatcaccg ggatcgggga ggagctatgg cggtatcagg     4020
gggatgtagt ggtgcggaaa ttcccgtata acccgaatga tccgtactat gagatggagg     4080
gggatgcatg atgcacatgt agatagattt cctacaggcc gaatctgcat cggctccgtg     4140
acaaaaacaa ttttttttaaa agattaaaaa aagataaccc taatgagat atttggaaaa     4200 ataaaaaata aaaatacaag agaagactat ataaaagact aataataaaa tagagtagca    4260
```

```
gaatacctat tctaagtcac gttatctagg ggtcaggtga cacaaaagcc tttgcgggat    4320
tcatcccgca gaccctagaa cctactaagt agcgcactag acagcctaag atcaccgcgt    4380
gtgccttaca cctataaata ctaaaaatct taaaaataat aaactctaaa atagtgaaat    4440
atctatgtag taaaattaac aattaaccag agaatagaat aataactaaa gtataataga    4500
agtggaatat atatataata gacaagttcc gatgccgaat tgatagctct tgagagaata    4560
atcgaaatgg agatagaaag aagtaagcct agggtgtgta ataccagtgg cgtattggtc    4620
aatatctgat aattattgac tgagtccgga gtgttcgcac cagaatcggg agtcggagtc    4680
cacccgatgt cacgagaaca ggtacaaaga ggaagggatt gccccggtgg aggccagatt    4740
ctcaaagccc attccagctc aacgggtttg gtttgtttgc atgcgaccga ccattctaga    4800
cacggtcgcc aattcaaaga gcttctgctg ccaagattca cctataaata gaatctgtaa    4860
tcaagtaaga attaaaagtt gtatctatca ttatctatct ctatatcgca cttttcttgt    4920 aaaaccttc ccgtataaca catacaaaga aacgtaaat atcagagacc caggtatacc     4980
gtatatatta agccaagagc gccgtgtagt ggcgcttagt caatgtactt gggaagcgtc    5040
ttcaggatgc cgtcccgggc gatgtcctcc atcgctttgg tgatttcctg gaggaacctc    5100
ttgtcgccgc gcaagtcgtc accgaacagg ctcttgatgc tgaggagctc ggccgggctg    5160
gtgcctcctg cgcgagcctt ggcctggagc tcctcgcgca tcgggtcgtc gacctcgaac    5220
ttcttgccgc tgtcgtcgac gccgttaatg taatggaacc aggcagccgc aacgaaacac    5280
aggcggcgga atgggccagt aacccagatc gcctcagcaa tcgaaggcat gataaattgt    5340
gggatcttgc ccgaagcgtt gaggcagatg cggggcagtt ggtccatgat ggtgggttg     5400 gagaagcgct cgatgagcgt cttgcaatac tcatcaatgt tgacgcccgg gatctcgggc    5460
aacaacggct tcacctcgtc ctgcatcatt tgccacacaa acttgctgaa cagtgggttc    5520
tccatcacct cgtggacata tttgaagccg gccagctgcc ctgggtagcc gatggccgag    5580
tggctgccgt tgagcaggcg cagcttgtgc ttctcgaatt cctcgacgtc atggacattc    5640
ttgaccacct gggcaccaac cttctcgaat ggtgggcggc catcggagaa ctgatcctca    5700
attacccact gcataagggg ctctgtgacg acgggccacg agtcctcgat ggcaaagttg    5760
tctgcgagtg ccgttttatc ggtggcggat gtctgagggg tgatacggtc gaccatggcg    5820
ttggggaagg cgccctgttc ggcaatccac ttcgcgatct cggggttgcg caggcgcgca    5880
aaggactcga gcatgtggcg agtgatgaa ccgttcttct gcatgttgtc acacgacatg     5940
acggtaaagg gcttgagccc ttgctggtag cggcgtgcca gagcggcata gaggaagccg    6000
aacgtggtgc gcggggactt ctcgttcgct ggttggaggt cgaactgaat gtcagggtgc    6060
tcactttgga gctcgtgtgt gttctcgttg tagtagtaac cgctctcggt gatagtgagc    6120
gacacaatgt gggtatccgg gtgcgccatc ttggcgatga cggcctcgcg gttatcgggg    6180
gcaaagagat aggaattgat gctcccaaca acatgggcaa agctgccctt ggccgaacgc    6240
tcaatgacgg tgtagaggtg gtcctgcgac cctaaggcgt cgcgcatggc ggcgtcaaag    6300
ggctgcaaac caacaccaca aatcgcgtag tcagtcacac catgcttctg catcaactgg    6360
tcgacataaa cggccaagtg agctctgtgg aagccgccga cgccgacgtg gacaattccc    6420
tccttcacgt cgccaccacg cttgtaggtt gggaccttga cttgggtctc acctgccgcc    6480
gcaatttgcg acaggttttt gttgttgagc ttcaggggag ccattgtgaa tgtgtgaaga    6540
gtgagagaga ggaattgaaa gaaagacaag ggcgagaagg cgagagagaa aaggggggttt   6600
```

-continued

```
gttgttttttt ttctggctgg ggcgctgagt cgacgagggt caccgccagt ttttgaccgc    6660
tggttggaac agattacatc atgtggtggg gagctgatct cacgaggttc tcgaattttt    6720
ttagccactt gataaaaaaa aatcaaaagt acagtgcaat tagataagca ttccttttt     6780 cttttttat ttcttggttg ccgctctcgg tcgccgtatc acattttaaa ctcaacgtgc     6840
ttaaggtttt catgttcgaa gtcaccttt gtcaatggaa caaaaagaaa aactctgaga    6900
tccacccaca taaaaccta aaagaagtca gctgttgaaa atgaacaaag atatagatct    6960
```

<210> SEQ ID NO 11
<211> LENGTH: 23
<212> TYPE: DNA
<213> ORGANISM: Artificial Sequence
<220> FEATURE:
<223> OTHER INFORMATION: primer

<400> SEQUENCE: 11
tagcaccatc tactctgagt ggc                                              23

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
cctggtcata tagtcgtagt tgc                                              23

<210> SEQ ID NO 13
<211> LENGTH: 18
<212> TYPE: DNA
<213> ORGANISM: Artificial Sequence
<220> FEATURE:
<223> OTHER INFORMATION: primer

<400> SEQUENCE: 13
gctagcttat actaaccc                                                    18

<210> SEQ ID NO 14
<211> LENGTH: 18
<212> TYPE: DNA
<213> ORGANISM: Artificial Sequence
<220> FEATURE:
<223> OTHER INFORMATION: primer

<400> SEQUENCE: 14
gactatgttc tcgtgcgc                                                    18

<210> SEQ ID NO 15
<211> LENGTH: 18
<212> TYPE: DNA
<213> ORGANISM: Artificial Sequence
<220> FEATURE:
<223> OTHER INFORMATION: primer

<400> SEQUENCE: 15
tctttgcatt tgtccagg                                                    18

<210> SEQ ID NO 16
<211> LENGTH: 18
<212> TYPE: DNA
<213> ORGANISM: Artificial Sequence
<220> FEATURE:
<223> OTHER INFORMATION: primer

```
<400> SEQUENCE: 16
tctgcgtcgt tggacaac                                              18

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
gactgaccct cattatgc                                              18

<210> SEQ ID NO 18
<211> LENGTH: 18
<212> TYPE: DNA
<213> ORGANISM: Artificial Sequence
<220> FEATURE:
<223> OTHER INFORMATION: primer

<400> SEQUENCE: 18
aacaccgagg gaccatgg                                              18

<210> SEQ ID NO 19
<211> LENGTH: 18
<212> TYPE: DNA
<213> ORGANISM: Artificial Sequence
<220> FEATURE:
<223> OTHER INFORMATION: primer

<400> SEQUENCE: 19
tacctcaccc tccgatcc                                              18

<210> SEQ ID NO 20
<211> LENGTH: 18
<212> TYPE: DNA
<213> ORGANISM: Artificial Sequence
<220> FEATURE:
<223> OTHER INFORMATION: primer

<400> SEQUENCE: 20
gggacagcac acctgacg                                              18

<210> SEQ ID NO 21
<211> LENGTH: 18
<212> TYPE: DNA
<213> ORGANISM: Artificial Sequence
<220> FEATURE:
<223> OTHER INFORMATION: primer

<400> SEQUENCE: 21
aacccgaatg atccgtac                                              18

<210> SEQ ID NO 22
<211> LENGTH: 18
<212> TYPE: DNA
<213> ORGANISM: Artificial Sequence
<220> FEATURE:
<223> OTHER INFORMATION: primer

<400> SEQUENCE: 22
agagaataat cgaaatgg                                              18

<210> SEQ ID NO 23
```

```
<211> LENGTH: 24
<212> TYPE: DNA
<213> ORGANISM: Artificial Sequence
<220> FEATURE:
<223> OTHER INFORMATION: primer

<400> SEQUENCE: 23
tggctgaacc tggggatgca ccac                                           24

<210> SEQ ID NO 24
<211> LENGTH: 9135
<212> TYPE: DNA
<213> ORGANISM: Aspergillus oryzae

<400> SEQUENCE: 24
tggccaccgt ggtggcttaa actaccggag ttttacagta ggaacatcag ggggtaacag     60
aaacattttt gcttttggac caacggcatt cggatcggga taccgacttt agcagggtat    120
atcctcatgc ggtccacgga agagggttga aaagtatcat aagttattgt cattattttc    180
cttcagaagg tggaatggaa tcaagtcaaa cactattcat agctttaagg aagagtactt    240
ttggtataaa aactaacttg ggatacctct tactgccgtc gcggagggtc caggacggga    300
cgatccgaag acgaacatcc tccagctcgt gtatcagtgg ctgtaatgaa cgagggccat    360
tagtgaggca tggatcaatc ctgctcacat cgcgaaatgc tccggcggca cggaatctgg    420 tggggggcgat attacttgct aaacatcctc acttgtggcc ttcgtacagt ttgctttgaa    480
caccttatct ccactaaaaa gagctcaaat gatggattct catatcgggg actgccaggt    540
aatatagata gtataccagc gaatcagtca agctcctcga gcgagagagt tagccaatcc    600
gactacggaa aggagctact gtggtcacaa tgcagcgaga tacccccaccc ttggcaattg    660 aattagccct ctataacaaa gctgcgagtt ggtacttacc tttttttttt tttaaaaaaa    720
aaaaaactgt atttgtcttt atacaaagta ttgctatcgc tttaccagca gagcttgacc    780
aaaatgtccc tagaattcca gcgtatagag agatctcgct ttttaaagtt cgtacagttc    840
ccactttttc attactcggt caacagcttt gctagcttat actaacccag tgaatcaaac    900
aatcgataat gtattgacag agctgtctgg aaggatggaa ataatataca acaaaagtac    960
cgttctcaac tctcactgct caaagcccgc ccatgtcctc cacccttagcg agcacctcgt   1020 cacccaaaaa gagcagacca catcctgaaa cgatgcccct caagatcgaa acaactaccc   1080
tcctctacta gcgtacatct tctctaacaa ttttctctca tataacctag atcaacaatg   1140
gcaggcattc ttcgagtgga agaattcaca cgctatccgc ttaatccgag ataagttccg   1200
atactgtggt cttcgaagtc ttcacaatag ggcatagcct tccaaggatt ggaattatag   1260
ggataataca taagaattat agctagggta tcagaggagt tacttcgctc cttagagaga   1320
gcacttaccc gagccaaata ccaaggatag aaatgattag aagatagact atgttctcgt   1380
gcgcttagcc cctatgatt atgtttctca atttcgcatc atttcagggt attggcgttc    1440
ctccagtaaa cgagggtaa actattctgc tagtttgatg gtcgcttata ggctgaagat   1500
aaccaacaag aagatacact tcgcttagat cctcgaccat ggtgagcagc cactctgtcc   1560
aactttctga aatggcggtg ctaagtatag aacttgatg atgcaatgac tacaacaagc   1620
atcaaaagac cgataaacag cctcggcaaa gcccagcgat caacctctgt ctccaaactg   1680
gcatactatg caagtctaac catagtgaaa tactatcaga cgaagtacat catgtatttc   1740
atagataaag ctcatgctat ggaacaatta catctcaaca cttctttcat tgaagctgtg   1800
acttgatgcc tccgttgctt tgcagcagag atatgtcccg atacttccgt gacctttgtt   1860
```

```
tctctttgca tttgtccagg gactgtctcc ccgcagggtc tatcaacgtg ggacgcgata    1920
agccccattc ttgacaactg aacggattcg ctggagataa tcgcaaccgg ttccgatctc    1980
atcttcatat acaaagcacg gtcacgctaa atctctacga ggcccaaccg tatggaaaaa    2040
tatcgctacg ggctgaatgt atgggtcttg gatctatgc taagtcattg tatccagtga     2100
gagcatctgc atcattgaca tttccgcctg taccttctgg tttaggaaaa ttcaacagcg    2160
ggctgacgcg atgcacctgg cgggttatgg tattaggaat cgaagagtga tgaaaatagt    2220
tgacaagaca gtctgatatt ggctgagatg atactcttta ttaaatttta gcttagctag    2280
ttccgagcag gccgaatgag acaagtataa agccatgacc ctggcactta atctcgtccg    2340
tctcacaaca gccagtgttt tctgcgtcgt tggacaacat gaggctaacg atctccgcgg    2400
cagtattgcc ttcgttgctt cttctcccct gcttcttagg agatgctcta gctcatccga    2460
gacctgatcc taagacagca tgggtgcgtc aaggtcggag aaggaagagt tccccgcgga    2520
acctgcaagt ccattcgtct atgctctcga cctgcgtcga gagcaatgcc actgtgatca    2580
aagcacccaa gcataatgtt tgggaaggca tgacggacga ggaaacagcc tctgtggtta    2640
agtggctctt ccaacaaccg acgctgaacc tgactgtcac ggaaggcgcc ggagagtggg    2700
ataacacgat gtaagcgcca ctttcggat cactctcggt ggctaacagg accagtgccc      2760
tcgtcgagct gatgcgcccc aacaagacgg atgttttaag ctatctcgat caccaaggcc    2820
cagcacctag ccgttacgcg catgttgtcc ttgacaaccg cgccacgact gaccctcatt    2880
atgctgatct tttggtcggg cctctagcca tcaccaatca gtctacccct tcttggacgc    2940
cattagagta tccttacacg cgcaagactc acggtcgagt gcgcaatctc gacgctgact    3000
atagcaccat ctactctgag tggctgtata agattagcgc atccattgca gatatcaccc    3060
tggacctgtt caatgggact gcattgggct tagacaacga cactcttgat atatggggga    3120
ttgaccccct ctggcaggat gacggccgga tcatccgctg ggacacattc tggaacatgc    3180
caacggatga gttcgacacc ggcagcatcc taccgctggg actattcttc aaatccgacg    3240
tgactgggcg tgatccttct cagtggaagc ttgaaggctg gctttacaac gacatcttct    3300
atgaaacgac agaggctttt cgccatgcat tcttctcgac cggatttgtc aagctaaagc    3360
ccaacaccga gggaccatgg gcgcagacgg accaacgggg ccctatactt ccacaagaca    3420
agcagcaatc gcctctcatg gtagcgccgt caggagcacg gtactctgtg gacctcgacc    3480
gcaaatacgt gacatggatg gacttctcgt tttacatcag cttctctcgt gataccggcg    3540
tatcagtgtt tgatatccgc tataaaggtc agcgcgtgct gtacgagttg ggtctacaag    3600
aggcactcgc ccactatgcg ggcaacgatc caatccaatc cagcgtcgca tatctggact    3660
catactacgg ctttggaccg tacgcctttg agctagtcaa aggctacgac tgtccggtct    3720
atgcaaccta cctcaacagc tccttctacg tttccgagac aacacacacg cacattgaca    3780
gtctctgtgt gtttgagtac gatgccgact atcctattca gcgccacagc acgtccgact    3840
acgtcagcag tacgaagaac gtatacctca ccctccgatc cgtgtccacg atcggcaact    3900
acgactatat gaccaggtga gttccacgcc ccgaaagacg catgaaatca cacccatta     3960 accatgcttc cagctacacg ttccacatgg atggcacgat tggcgtcgaa gtccgcgcct    4020
ccggctacat ccaagccgcc tactacgcgc acaacgaaga cttcggctac cgcatccacg    4080
atgcgttgtc cggcagcatg cacgaccacg tcctcaactt caaggccgac ttcgacatcc    4140
tcggcgtgaa caacagcatc gagctcacta cggtggcccc ggtcacccgc accttcacct    4200
```

```
ggtccggcgg ccgctcgcgc aacaccatga ccctggaacg gtccatccta tcgtccgaag    4260
acgaaggccg cttcaactgg ggccccaacg gggcgacgat gatgcacgtc atcaaccagg    4320
acgcccgcaa cccgtacggc gagtaccggg gctaccgcgt gctgccggcg gccgggacag    4380
cacacctgac ggtccaggac tccagcaacc tggcgcacgc ggcgcactgg gccgagtacg    4440
acatccaggt cacgcggcag cacgaccacg agccgcgcgc cgcgcacgcc tacaacagcc    4500
aggacatcca aacccgccc gtcaacttcg ccgagttctt cgacggcgag ccgctcaacc    4560
agaccgatct ggtcgtgtgg ctgaacctgg ggatgcacca cgtcccgcac acgggcgacc    4620
tgccgaacac ggtgttcacg acggcccgct ccggggtgca gttcacgccg ctgaactacc    4680
tcgccgggga cccgagccgg cagacggtga acatggtgcg agtgaattat gcgaatgggt    4740
cggcgacgga ggtgaagacg ttcgggcagg cggaggaggt ctgtacggta cccatcaccg    4800
ggatcgggga ggagctatgg cggtatcagg gggatgtagt ggtgcggaaa ttcccgtata    4860
acccgaatga tccgtactat gagatggagg gggatgcatg atgcacatgt agatagattt    4920
cctacaggcc gaatctgcat cggctccgtg acaaaaacaa tttttttaaa agattaaaaa    4980
aagataaccc taatggagat atttggaaaa ataaaaaata aaaatacaag agaagactat    5040
ataaaagact aataataaaa tagagtagca gaatacctat tctaagtcac gttatctagg    5100
ggtcaggtga cacaaaagcc tttgcgggat tcatcccgca gaccctagaa cctactaagt    5160
agcgcactag acagcctaag atcaccgcgt gtgccttaca cctataaata ctaaaaatct    5220
taaaaataat aaactctaaa atagtgaaat atctatgtag taaaattaac aattaaccag    5280
agaatagaat aataactaaa gtataataga agtggaatat atatataata gacaagttcc    5340
gatgccgaat tgatagctct tgagagaata tcgaaatgg agatagaaag aagtaagcct    5400
agggtgtgta ataccagtgg cgtattggtc aatatctgat aattattgac tgagtccgga    5460
gtgttcgcac cagaatcggg agtcggagtc caccgatgt cacgagaaca ggtacaaaga    5520
ggaagggatt gccccggtgg aggccagatt ctcaaagccc attccagctc aacgggtttg    5580
gtttgtttgc atgcgaccga ccattctaga cacggtcgcc aattcaaaga gcttctgctg    5640
ccaagattca cctataaata gaatctgtaa tcaagtaaga attaaaagtt gtatctatca    5700
ttatctatct ctatatcgca cttttcttgt aaaacccttc ccgtataaca catacaaaga    5760
aaacgtaaat atcagagacc caggtatacc gtatatatta agccaagagc gccgtgtagt    5820
ggcgcttagt caatgtactt gggaagcgtc ttcaggatgc cgtcccgggc gatgtcctcc    5880
atcgctttgg tgatttcctg gaggaacctc ttgtcgccgc gcaagtcgtc accgaacagg    5940
ctcttgatgc tgaggagctc ggccgggctg gtgcctcctg cgcgagcctt ggcctggagc    6000
tcctcgcgca tcgggtcgtc gacctcgaac ttcttgccgc tgtcgtcgac gccgttaatg    6060
taatggaacc aggcagccgc aacgaaacac aggcggcgga atgggccagt aacccagatc    6120
gcctcagcaa tcgaaggcat gataaattgt gggatcttgc ccgaagcgtt gaggcagatg    6180
cggggcagtt ggtccatgat ggtggggttg gagaagcgct cgatgagcgt cttgcaatac    6240
tcatcaatgt tgacgcccgg gatctcgggc aacaacggct tcacctcgtc ctgcatcatt    6300
tgccacacaa acttgctgaa cagtgggttc tccatcacct cgtggacata tttgaagccg    6360
gccagctgcc ctgggtagcc gatggccgag tggctgccgt tgagcaggcg cagcttgtgc    6420
ttctcgaatt cctcgacgtc atggacattc ttgaccacct gggcaccaac cttctcgaat    6480
ggtgggcggc catcggagaa ctgatcctca attacccact gcataaaggg ctctgtgacg    6540
acgggccacg agtcctcgat ggcaaagttg tctgcgagtg ccgttttatc ggtggcggat    6600
```

```
gtctgagggg tgatacggtc gaccatggcg ttggggaagg cgccctgttc ggcaatccac   6660
ttcgcgatct cggggttgcg caggcgcgca aaggactcga gcatgtggcg agtgatggaa   6720
ccgttcttct gcatgttgtc acacgacatg acggtaaagg gcttgagccc ttgctggtag   6780
cggcgtgcca gagcggcata gaggaagccg aacgtggtgc gcggggactt ctcgttcgct   6840
ggttggaggt cgaactgaat gtcagggtgc tcactttgga gctcgtgtgt gttctcgttg   6900
tagtagtaac cgctctcggt gatagtgagc gacacaatgt gggtatccgg gtgcgccatc   6960
ttggcgatga cggcctcgcg gttatcgggg gcaaagagat aggaattgat gctcccaaca   7020
acatgggcaa agctgcccct tggccgaacgc tcaatgacgg tgtagaggtg gtcctgcgac   7080
cctaaggcgt cgcgcatggc ggcgtcaaag ggctgcaaac caacaccaca aatcgcgtag   7140
tcagtcacac catgcttctg catcaactgg tcgacataaa cggccaagtg agctctgtgg   7200
aagccgccga cgccgacgtg gacaattccc tccttcacgt cgccaccacg cttgtaggtt   7260
gggaccttga cttgggtctc acctgccgcc gcaatttgcg acaggttttt gttgttgagc   7320
ttcaggggag ccattgtgaa tgtgtgaaga gtgagagaga ggaattgaaa gaaagacaag   7380
ggcgagaagg cgagagagaa aaggggggttt gttgttttttt ttctggctgg ggcgctgagt   7440
cgacgagggt caccgccagt ttttgaccgc tggttggaac agattacatc atgtggtggg   7500
gagctgatct cacgaggttc tcgaattttt ttagccactt gataaaaaaa aatcaaaagt   7560
acagtgcaat tagataagca ttcctttttt cttttttttat ttcttggttg ccgctctcgg   7620
tcgccgtatc acatttttaaa ctcaacgtgc ttaaggtttt catgttcgaa gtcacctttt   7680
gtcaatggaa caaaagaaa aactctgaga tccacccaca taaaacccta aaagaagtca   7740
gctgttgaaa atgaacaaag atatagatct ctggtattaa attcccatca tacctgaccc   7800
caattcaagc caaaattcgg gcaataaggg gaaaacaccg acggcaggct ggaatcatct   7860
tggttgcgat gatggcaaag tatcggggac actccacaac cccagtacct ccctggaccc   7920
acgaagaggc cggggcaacc cactgagcca tagaacatga tcgaagcctc ccccgaatcc   7980
tgtcattgtt gtcaatcacc gtgggaactc gtgtgtttgg acggaccaaa gtgggcagga   8040
gctgatcggg ccgagaccgt attggtagca aggagtgggt tcctggcaat gaacccacat   8100
gacctgggtc agagggacga gcacggttgg tattcccatg atgggggtgg ctcctgcgac   8160
cctcttccca tcgatcccaa taaattgccc agtatcatat cggtctcccc gagggcgact   8220
attgaagtat ccctgagcat agtctcgtgg ctagtaacta gtatagactg gctatacaca   8280
tcatcatcat cacaccggga tttccgacaa ggctcgcaag aggtggtctt tccatttgcg   8340
gcgtcgcgag tttctggtac ggtttcagca tcacaaagat atgaggggggg ttgatgggat   8400 gctatatacg tatttgttag tgtaaaaatt tccgatcgga gattccaagt gaggtatgac   8460
tgctgattga tctcctagga ggtattaaga agggaagtta ttttgttcta ctatgagggg   8520
ttctgtacac aaccctctc accagatacc cacgtgaccg tcggccgagg tcttgtcagg   8580
tgcattcaat tgccacgtat tacatctgct acctccaccg cttatccact gcatattcct   8640
catgactcgc gtggatgtga catgtaaccc tgtgtgcatt tttacccgat acccttttct   8700
gcaaattatt gacacctatc gacgcccgca tcaaagtcgg cgaacaacct tatcggatgc   8760
aggggtggct tcgatagcga catgcatagg tgtcagtcgg aagtctctcg tgacctgaag   8820
cggtgtgcgt ttgttatcat tttgagcttg caagtcaatt ccatgctcca ataaggttac   8880
gccaaacatc tcgttgtcaa ccgtgacaca ctagtgcaaa atcatggact actcaatgcc   8940
```

-continued

```
cgatatcgcg taaccagctg cccatgacgg actcctatct ccaagaatct cctaaagatc    9000
gacagtattc atgctcactc gtacactttg tttcagccaa cgggtgacaa ctcggagcca    9060
tttctttgac gttgtcatcc aagattaagc ttgcatcgtc ggaaggaggc atgtgcgtca    9120
atgcctcttt ggcca                                                     9135
```

FUNGUS-ORIGIN LYSYL OXIDASES

TECHNICAL FIELD

The present invention relates to lysyl oxidase derived from filamentous fungi and DNA encoding the same, and uses thereof.

BACKGROUND ART

Among the filamentous fungi, in particular, *Aspergillus* including *Aspergillus oryzae* (yellow *Aspergillus*) etc. has been traditionally used in brewing industry in Japan for producing sake, bean paste, soy sauce, mirin, and the like, and directly eaten. *Aspergillus* is a safe source of genes listed up in GRAS (Generally Recognized as Safe) of US FDA (Food and drug Administration).

Therefore, in the safety test such as a chronic toxicity test required when genes derived from general fungi are used for foods, etc., in the case of genes derived from general fungi, the cost is about 1 billion yen. On the other hand, in the case of genes that are the above-mentioned GRAS genes, it is advantageous that the cost can be made to be about one-third of the cost and further that it takes a shorter time to conduct the test as compared with the case of general genes.

Thus, filamentous fungi, in particular, *Aspergillus* could provide a treasure trove of genes with a high utility value from the safe and economical viewpoint. The technology related to the present invention is disclosed in Japanese Patent No. 2796114 (patent document 1) and Japanese Patent No. 2977245 (patent document 2).

DISCLOSURE OF INVENTION

Therefore, by clarifying information on the genome DNA of these fungi and clarifying the functions of genes encoded thereby, it is possible to provide an effective using method of safe gene resources, for example, production of materials with the use of biotechnology, in food industry; and to provide useful information for screening various kinds of genes in the field of agricultural chemicals and medicine.

Furthermore, it would provide a useful tool for analyzing genome information of grain contamination fungi such as closely-related species including for example, *Aspergillus flavus, Aspergillus fumigatus*, etc. and human-infecting bacteria.

As a result of investigation with the view of the above-mentioned object, the present inventors have succeeded in analyzing the genome of *Aspergillus oryzae*, that is, a kind of *Aspergillus* and have determined the base sequence thereof (and an amino acid sequence encoded by the base sequence) and various functions etc. Based on such results, the present inventors disclosed various DNAs derived from *Aspergillus oryzae*, as well as a primer set for amplifying a gene of filamentous fungi in GRAS grade including a nucleotide sequence prepared by these DNAs and a probe for detecting genes of filamentous fungi, etc. in the prior application (JP2001-403261).

The present inventors have conducted a further investigation based on the resultant genome information on *Aspergillus*. That is to say, the present inventors paid attention to lysyl oxidase and identified a sequence encoding lysyl oxidase from the resultant base sequences. The present inventors have also tried to identify an amino acid sequence of a protein encoded by the sequence. Note here that lysyl oxidase is a kind of amine oxidase and has a function of oxidizing lysine residues in protein so as to crosslink the lysine residues. The presence of lysyl oxidase derived from animals has been traditionally known and such lysyl oxidase has been applied to improving the texture foods (see for example the above-mentioned patent documents 1 and 2). In recent years, studies on lysyl oxidase derived from microorganisms has been conducted and lysyl oxidase having a substrate specificity similar to lysyl oxidase derived from mammals has been found from *Pichia Pastoris*, a kind of yeast (FEBS Lett. 1988 238, 74-76). It was found that this lysyl oxidase derived from *Pichia Pastoris* not only had a property similar to that of lysyl oxidase derived from mammal but also had a structure similar to that of amine oxidase of bacteria such as *Escherichia coli, Arthrobacter globiformis* etc. (see J. Inorg. Biochem. 2001 83 (2-3): 193-204). However, the isolation of lysyl oxidase from filamentous fungus that is a higher microorganism likewise yeast has not been reported to date.

The preset inventors have investigated earnestly and successfully found a sequence, which is highly homologous to lysyl oxidase genes derived from the already reported *Pichia Pastoris*, in genome of the *Aspergillus*. When expressing a protein encoded by the base sequence by using a filamentous fungus as a host, the lysyl oxidase activity was shown. From the result, it was experimentally confirmed that the sequence encoded lysyl oxidase. On the other hand, the present inventors have succeeded in identifying the coding region in the sequence and have found that a protein encoded by the sequence has a novel amino acid sequence. Thus, the present inventors succeeded in identifying lysyl oxidase derived from filamentous fungi and the amino acid sequence thereof for the first time.

The present invention was completed based on the above-mentioned results and the specific object of the present invention is to provide lysyl oxidase derived from filamentous fungi and a DNA encoding the same, and a method for producing lysyl oxidase derived from filamentous fungi. In order to achieve the objects, the following configurations are provided.

[1] Lysyl oxidase consisting of a protein described in the following (a) or (b):
  (a) a protein having an amino acid sequence set forth in SEQ ID NO: 2; or
  (b) a protein having an amino acid sequence configured by modifying a part of the amino acid sequence set forth in SEQ ID NO: 2, and functioning as lysyl oxidase.

[2] A DNA described in the following (A) or (B):
  (A) a DNA encoding lysyl oxidase described in [1]; or
  (B) a DNA which hybridizes under stringent conditions to the DNA described in (A) and encodes a protein functioning as lysyl oxidase.

[3] A DNA having any one of the following sequences (i) to (iii):
  (i) a base sequence of SEQ ID NO: 3;
  (ii) a base sequence of SEQ ID NO: 4;
  (iii) a base sequence of SEQ ID NO: 5;
  (iv) a base sequence of SEQ ID NO: 6;
  (v) a base sequence of SEQ ID NO: 1; and
  (vi) a base sequence of SEQ ID NO: 7.

[4] A vector carrying the DNA described in [2] or [3].

[5] Filamentous fungi into which the DNA described in [2] or [3] is exogenously introduced.

[6] A method for producing lysyl oxidase, the method including the following steps (1) and (2):
  (1) a step of culturing the filamentous fungi described in [5] under conditions where a protein encoded by the DNA can be produced; and
  (2) a step of collecting the produced protein.

The "DNA" of the present invention is not limited to a double strand DNA but is intended to include a single strand DNA (sense chain and antisense chain) constituting the double strand DNA. Furthermore, the DNA of the present invention includes a DNA having an arbitrary base sequence considering the degeneracy of codons. Furthermore, the form of the DNA is not limited and may include a cDNA, a genome DNA and a synthetic DNA.

The "DNA encoding a protein" of the present invention is a DNA from which a protein is obtained when it is expressed. The "DNA" includes not only a DNA having a base sequence corresponding to an amino acid sequence of the protein but also a DNA obtained by adding a sequence that does not encode an amino acid sequence to the DNA having a base sequence corresponding to an amino acid sequence of the protein (examples of the latter DNA includes a DNA including one or a plurality of introns).

The "Lysyl oxidase derived from filamentous fungi" of the present invention includes lysyl oxidase prepared by using filamentous fungi as a starting material or lysyl oxidase prepared by using information (amino acid sequence or DNA sequence) of lysyl oxidase carried by filamentous fungi in the process of obtaining lysyl oxidase. Examples of such lysyl oxidase include not only a lysyl oxidase prepared from filamentous fungi by using a physical technique, a biochemical technique and the like but also lysyl oxidase prepared by a gene engineering technology using an amino acid sequence or a DNA sequence of the lysyl oxidase disclosed in the present invention.

BRIEF DESCRIPTION OF DRAWINGS

FIG. 3 shows a sequence of a 3' DNA fragment amplified by using a primer specific to the gene in which RNA extracted from a transformant carrying a lysyl oxidase gene is used as a template. An underlined part shows the position of the primer (LO-3') used herein.

FIG. 4 is a schematic view showing a procedure for constructing a vector pBALO-D.

Figure 1:
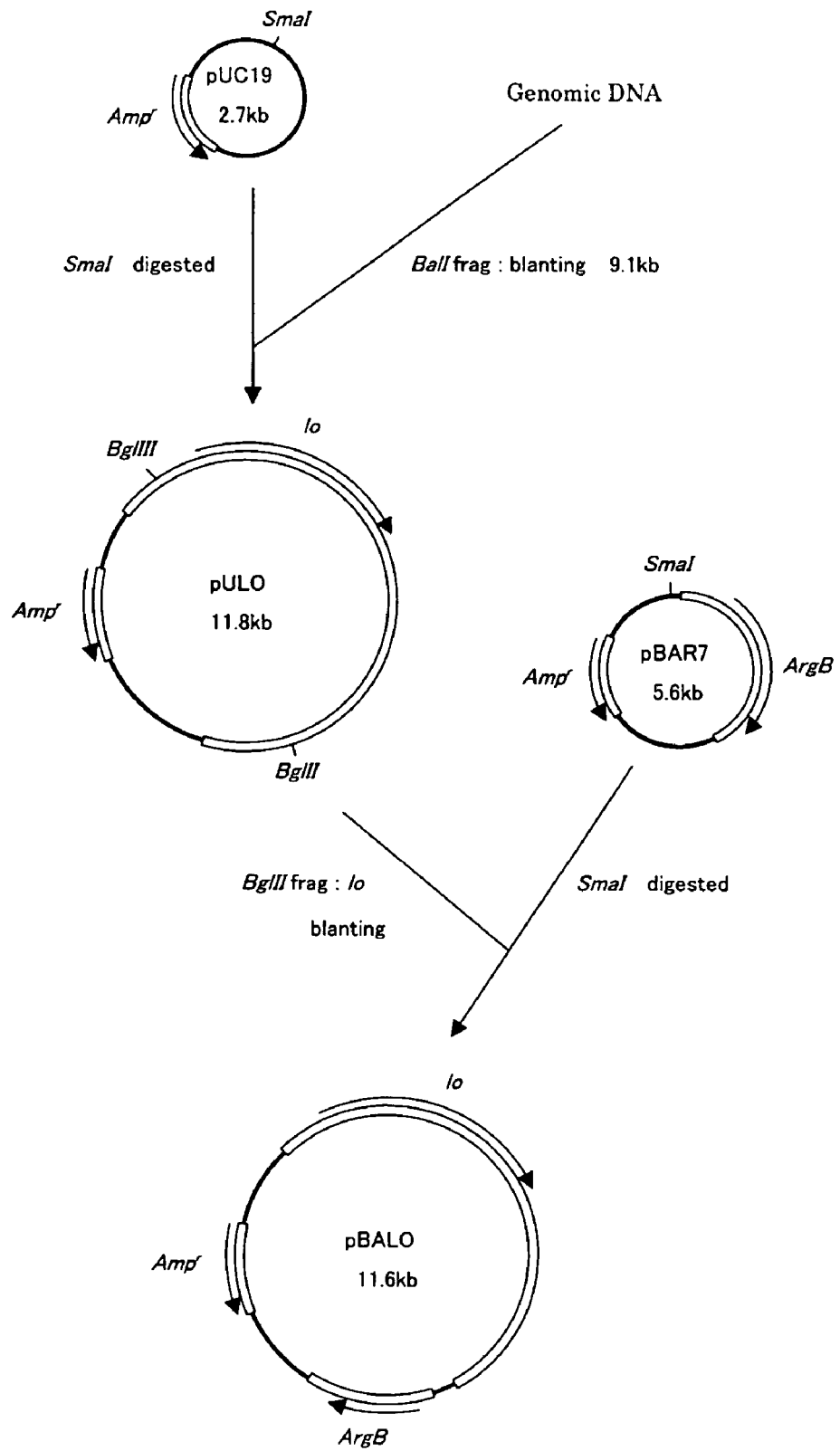
FIG. 1 is a schematic view showing a procedure for constructing a vector pBALO.

BEST MODE FOR CARRYING OUT THE INVENTION (Protein)

The first aspect of the present invention relates to lysyl oxidase derived from filamentous fungi. Lysyl oxidase provided in the present invention includes a protein having, for example, an amino acid sequence set forth in SEQ ID NO: 2. As shown in the below-mentioned Examples, it has been confirmed that the protein actually exhibits a lysyl oxidase activity in the expression system using filamentous fungi.

Herein, in general, in a case where a part of the amino acid sequence of a protein is modified, a protein after modification has the same function as that of a protein before modification. That is to say, modification of the amino acid sequence may not substantially affect the function of the protein and the function may be maintained before and after modification. Taking this fact into consideration, a protein obtained by modifying a part of the amino acid sequence (SEQ ID NO: 2) of the protein having the above-mentioned lysyl oxidase activity (hereinafter, the protein will be referred to as a "modified protein") may constitute the lysyl oxidase (protein) of the present invention as long as the function as lysyl oxidase is maintained. In other words, as long as the function as lysyl oxidase is maintained, a part of the amino acid sequence allowed to be modified. Note here that it is preferable that the lysyl oxidase activity is not decreased as a result of modification, however, somewhat fluctuation (increase or decrease) of the lysyl oxidase activity is allowed.

The phrase "a part of an amino acid sequence is modified" herein is intended to mean that one or a plurality of amino acids in the amino acid sequence are deleted, substituted, added and/or inserted. The position of the modification (mutation) of the amino acid sequence is not particularly limited as long as the lysyl oxidase activity is maintained. Furthermore, modification may be conducted at a plurality of positions. The number of amino acids to be modified may be, for example, the number corresponding to 10% or less of the entire amino acids, preferably the number corresponding to 5% or less of the entire amino acids, and further preferably the number corresponding to 1% or less of the entire amino acids. The above-mentioned modified protein can be formed by a genetic engineering technique, for example, by preparing a nucleic acid fragment which has a sequence obtained by modifying a base sequence coding the amino acid sequence of SEQ ID NO: 2 and makes this fragment to express in a suitable expressing system.

Among the protein (including modified protein) of the present invention, the protein of natural filamentous fungi can be prepared by operations such as extraction and purification from the filamentous fungi. Furthermore, the protein (including modified protein) of the present invention can be prepared by the genetic engineering technique based on information of lysyl oxidase disclosed herein. For example, a DNA encoding the protein of the present invention is used so as to transform an appropriate host cell and proteins expressed in the transformant are collected, to thus prepare the proteins of the present invention. The collected proteins are appropriately purified in accordance with the purposes. In a case where a protein is prepared as a recombinant protein, various modifications can be conducted. For example, when DNA encoding the protein of the present invention and other appropriate DNA are inserted into one vector and the vector is used so as to produce a recombinant protein, a recombinant protein in which the protein of the present invention is linked to other peptide or protein can be obtained. With such a modification, it is possible to simplify extraction and purification of a recombinant protein or to add the biological functions thereto, and the like.

(DNA Encoding Lysyl Oxidase)

According to a second aspect of the present invention, a DNA encoding lysyl oxidase derived from filamentous fungi is provided. Specific examples of such a DNA can include a DNA having a base sequence of SEQ ID NO: 3 or SEQ ID NO: 4. The former is a sequence derived from a genome DNA (lysyl oxidase gene) encoding lysyl oxidase and the latter is a sequence of a genome DNA from which intron regions are excluded. Another specific example of the DNA of the present invention can include a DNA having a base sequence of SEQ ID NO: 5 or SEQ ID NO: 6. The former is a DNA having sequence including the lysyl oxidase gene set forth in SEQ ID NO: 3 and its putative promoter region. The latter is a DNA including DNA set forth in SEQ ID NO: 4 (DNA from which intron regions are excluded) and its putative promoter region. Since these DNAs have ideal combination of a promoter and a structural gene, if lysyl oxidase is produced by using the DNAs, excellent gene expression can be expected. Therefore, an efficient production system of lysyl oxidase can be constructed.

Further examples of the DNA of the present invention may include a DNA having a base sequence of SEQ ID NO: 1 or SEQ ID NO: 7. The former is a DNA having a sequence including the lysyl oxidase gene set forth in SEQ ID NO: 3, its putative promoter region and terminator region. The latter is a DNA set forth in SEQ ID NO: 4 (a DNA of lysyl oxidase gene from which intron regions are excluded), its putative promoter region and a terminator region. Also when such a DNA is used, an efficient production system of lysyl oxidase can be constructed.

Herein, since the putative promoter region in the sequences respectively set force in SEQ ID NOs: 1, 5, 6, or 7 is 1600 bp in length, which is long for a promoter region. Therefore, it is anticipated that a part of the region is directly involved in the promoter activity. From the viewpoint of this, a region including a continuous part in the putative promoter region (about 1600 bp at the side of '5) in these sequences can be used as a promoter of the DNA of the present invention as long as it is recognized to have a function as a promoter with respect to the lysyl oxidase gene. Therefore, by combining, for example, the thus identified promoter region and the structural gene of the sequence set forth in SEQ ID NO: 3, the DNA of the present invention (DNA encoding lysyl oxidase) can be formed. Herein, in general, from the viewpoint that a region functioning as a promoter is positioned immediately before the structural gene, a region including, for example, bases at positions 569 to 1568 and preferably bases at positions 769 to 1568 is a promising candidate of the functioning region.

The above-mentioned DNAs of the present invention can be prepared by appropriately using a probe, a primer, etc. capable of hybridizing specifically to a gene encoding the lysyl oxidase of the present invention (for example, a DNA having a base sequence of SEQ ID NO: 3) from an appropriate filamentous fungi genome DNA library or a cDNA library, or a cell extract of filamentous fungi. Note here that a production method of the genome DNA library of filamentous fungi or the cDNA library can be referred to, for example, Molecular Cloning, Third Edition, Cold Spring Harbor Laboratory Press, New York.

Specifically, the DNA of the present invention can be prepared by, for example, the following procedures. First of all, filamentous fungi which are expected to carry a targeted DNA are cultured for a predetermined period of time. And then filtration is conducted so as to collect fungi. The collected fungi are washed and then freeze-dried. Then, the fungus bodies are ground with the use of a mortar, etc. and an appropriate amount of extraction buffer solution (for example, SDS-containing Tris-HCl buffer solution) is added thereto so as to obtain an extraction solution. Then, a genome DNA is extracted and purified by phenol extraction, ethanol precipitation, and the like. By using the thus obtained genome DNA as a template, the PCR method is conducted by using a primer specific to the targeted DNA, so that the targeted DNA can be obtained as an amplification product.

The DNA of the present invention can be also prepared by using an appropriate filamentous fungi genome DNA library or cDNA library if it is available. In accordance with the kinds of libraries to be used, a plaque hybridization technique or a colony hybridization method can be used (see, for example, Molecular Cloning, Third Edition, Cold Spring Harbor Laboratory Press, New York). For example, in a case of the library constructed by using a plasmid, a colony hybridization method is used. For selecting a clone carrying the targeted DNA, a probe having a sequence specific to the DNA of the present invention is used. When the targeted clone is selected, PCR method, etc. using the DNA carried by this clone as a template is conducted by using a primer specific to the sequence of the targeted DNA, so that the DNA of the present invention can be obtained as an amplification product.

The DNA carried by the obtained clone can be subcloned into an appropriate vector so as to be used followingly. Thereby, for example, it is possible to construct a recombinant vector for transformation or a plasmid suitable for decoding a base sequence.

Herein, in general, in a case where a part of a DNA encoding a protein is modified, a protein encoded by the modified DNA may sometimes have the equivalent function to that of a protein encoded by the DNA before modified. That is to say, modification of the DNA sequence does not substantially affect the function of the protein encoded by the DNA and sometimes may maintain the function of the encoded protein before and after modification. Taking this fact into consideration, a DNA having a base sequence obtained by modifying a part of the above-mentioned DNA of the present invention (hereinafter, the DNA will be also referred to as "modified DNA") can constitute the DNA of the present invention as long as the protein encoded by the DNA has a function as a lysyl oxidase. In other words, as long as the function as lysyl oxidase of the encoded protein is maintained, a part the sequence is allowed to be modified. Note here that it is preferable that the lysyl oxidase activity is not decreased before and after modification, however, somewhat fluctuation (increase or decrease) of the lysyl oxidase activity is allowed.

Herein, "a part of . . . is modified" typically denotes that one or a plurality of bases are substituted, deleted, inserted, or added in the base sequence before modification. Such modification may be occurred in a plurality of sites. "A plurality" herein differs depending upon the position to be modified or kinds of modifications, but the plurality of numbers is, for example, 2 to 100, preferably 2 to 50 and more preferably 2 to 10. The above-mentioned modified DNA can be obtained by, for example, a treatment with a restriction enzyme; treatment with exonuclease, DNA ligase, etc; introduction of mutation by a site-directed mutagenesis (Molecular Cloning, Third Edition, Chapter 13, Cold Spring Harbor Laboratory Press, New York); random mutagenesis (Molecular Cloning, Third Edition, Chapter 13, Cold Spring Harbor Laboratory Press, New York), and the like. Furthermore, the modified DNA can be obtained by a well-known method using a mutation treatment, for example, treating filamentous fungi carrying a lysyl oxidase gene with ultraviolet ray, followed by isolating the modified gene.

Note here that the mutation by deletion, insertion, addition, or inversion, etc. of the bases as mentioned above may include naturally occurring mutation based on the individual difference, difference in species or genera of microorganism carrying lysyl oxidase, etc.

An example of a method for preparing the modified DNA can include a method including: extracting a genome (chromosomal) DNA from naturally occurring filamentous fungi (for example, *Aspergillus oryzae*) carrying a modified DNA; treating the extracted DNA with appropriate restriction enzymes; and then selecting and isolating a DNA that hybridizes under stringent conditions in a screening using a DNA of the present invention (for example, DNA having a sequence of SEQ ID NO: 3) or a part thereof as a probe. When a genome (chromosomal) DNA library including a clone carrying a modified DNA can be used, the modified DAN can be obtained by screening the library under stringent conditions using the DNA of the present invention (for example, a DNA having a sequence set forth in SEQ ID NO: 3) or a part thereof as a probe.

The DNA of the present invention may include a DNA that hybridizes to the DNA of the present invention (for example, a DNA having a sequence set forth in SEQ ID NO: 3 or a DNA obtained by modifying the DNA as mentioned above) under stringent conditions and encodes a protein that functions as lysyl oxidase. The "stringent conditions" herein denote a condition in which a so-called specific hybrid is formed and a non-specific hybrid is not formed. The stringent conditions fluctuate depending upon the length of the sequence or kinds of constituting bases. However, an example of the stringent conditions includes a condition in which a DNA is incubated in a hybridization solution (50% formaldehyde, 10×SSC (0.15 M NaCl, 15 mM sodium citrate, pH 7.0), 5×Denhardt solution, 1% SDS, 10% dextran sulfate, 10 μg/ml denatured salmon sperm DNA, 50 mM phosphate buffer (pH7.5)) at 42° C., followed by washing with 0.1×SSC and 0.1% SDS at 68° C. Amore preferable example of the stringent conditions can include a condition using a hybridization solution (50% formaldehyde, 5×SSC (0.15 M NaCl, 15 mM sodium citrate, pH 7.0), 1×Denhardt solution, 1% SDS, 10% dextran sulfate, 10 μg/ml denatured salmon sperm DNA, 50 mM phosphate buffer (pH 7.5)).

(Vector)

According to another aspect of the present invention, a vector carrying the DNA of the present invention (including a modified DNA) is provided. Such a vector is prepared by introducing the DNA of the present invention into an existing vector or a vector obtained by adding modification to the existing vector. Any vectors may be used as a starting material in principle as long as they can carry the DNA of the present invention, however, an appropriate vector can be selected in accordance with the purpose of use (cloning, expression of polypeptide), while considering the kinds of host cells. The introduction of the DNA of the present invention into a vector can be conducted by a well-known method using a restriction enzyme and DNA ligase (see, Molecular Cloning, Third Edition, 1.84, Cold Spring Harbor Laboratory Press, New York).

Note here that when a DNA that includes also a promoter region (for example, a DNA having a sequence of any of SEQ ID NOs: 1, 5, 6 and 7) is used, a recombinant vector may be constructed by incorporating a separately prepared promoter region and a structural gene (and a terminator) into a vector. In such a case, as long as a promoter function is appropriately exhibited, other sequences may be intervened between the promoter region and the structural gene (and the terminator) in the vector. Furthermore, a vector carrying the promoter region may be constructed firstly and then ligated to the structural gene.

Typically, a vector for transformation contains a lysyl oxidase gene (for example, a DNA having a sequence of SEQ ID NO: 3), a promoter and a terminator. In order to achieve an appropriate transcription of a structural gene by a promoter, a promoter, a gene of lysyl oxidase and a terminator are arranged successively from the upper stream toward the lower stream. A selection marker, a sequence having an enhancer function, and a sequence encoding a signal peptide may be contained in the vector.

(Transformant)

The vector for transformation can be used for transforming filamentous fungi. That is to say, by using the above-mentioned vector for transformation, a preparation method of the transformed filamentous fungi can be constructed. With such a preparation method, filamentous fungi into which the DNA of the present invention is exogeneously introduced can be obtained. The thus obtained transformed filamentous fungi can be used for production of lysyl oxidase. Specifically, by culturing transformed filamentous fungi into which the DNA of the present invention is exogeneously introduced under conditions where a protein (lysyl oxidase) encoded by the DNA, lysyl oxidase can be produced. Any appropriate culture media can be used in accordance with a host to be used. For example, various kinds of commercially available culture media or culture media to which ingredient necessary for growth, selection and promotion of expression of, for example, arginine, uridine, and the like are added can be used.

From the culture medium solution or fungus bodies after being cultured for a predetermined period of time, targeted protein (lysyl oxidase) can be collected. When the proteins are produced outside fungus bodies, the proteins can be collected from the culture medium solution and in other case, the proteins can be collected from fungus bodies. When the proteins are collected from the culture medium solution, for example, the targeted proteins can be obtained by isolation and purification by combining salting out such as ammonium sulfate precipitation, etc., dialysis, various chromatography, and the like. On the other hand, when the proteins can be collected from the fungus bodies, for example, the targeted proteins can be obtained by isolation and purification after the fungus bodies are ground by a pressure treatment, ultrasonic treatment, etc. Note here that after the fungus bodies are collected from a culture medium solution by filtration, centrifugation, etc. in advance, the above-mentioned series of steps (girding of fungus bodies, isolation and purification) may be conducted. Note here that since the lysyl oxidase of the present invention generally produced outside the fungus bodies, the isolation and purification thereof can be conducted relatively easily.

The kinds of host filamentous fungi to be used for transformation are not particularly limited. Examples of the host filamentous fungi include filamentous fungi classified in genera of *Aspergillus* (*Aspergillus oryzae*, *Aspergillus niger*, *Aspergillus nidulans*, *Aspergillus sojae*, *Aspergillus awamori*, *Aspergillus Kawachii*, *Aspergillus parasiticus*, *Aspergillus flavus*, *Aspergillus nomius*, *Aspergillus fumigatus*, and the like), *Penicillium*, *Trichoderma*, *Rhizopus*, *Mucor*, *Fusarium* or the like can be used. Preferably, filamentous fungi in *Aspergillus* genera is used. Among them, *Aspergillus oryzae* or *Aspergillus niger* is preferably used from the viewpoint of safety.

The vector for transformation can be introduced (transformed) into the host filamentous fungi by a well-known method. For example, it can be conducted by a method by Turner et al. using, for example, fungus body as a protoplast (see Gene, 36, 321-331 (1985)). Besides, a method by Gomi et al. (Agric. Biol. Chem., 51, 323-328 (1987)) may be employed.

Hereinafter, the present invention will be described in more detail with reference to Examples, but the present invention is not necessarily limited thereto. Note here that various kinds of genetic engineering techniques in Examples were conducted in accordance with the method described in Current protocols in molecular biology (edited by Frederick M. Ausubel et al., 1987) mentioned above.

EXAMPLE 1

Production Method of Whole-Genome Shotgun Library

1. Preparation of Insert Side
   (1) Obtaining of Chromosomal DNA
   Spores of filamentous fungi, *Aspergillus oryzae* RIB-40 strain (ATCC 42149) were inoculated in a YPD culture medium (0.5% yeast extract, 1% peptone and 2% glucose) and cultured over night with shaking at 30° C. Thereafter, a genome DNA was extracted in accordance with a method by Iimura (Argric. Biol. Chem. 323-328, 51 (1987)). A mitochondrial DNA mixed in the genome DNA was purified by cesium chloride ultracentrifugation so as to obtain only a chromosomal DNA in accordance with the method by Watson et al. (Methods Enzymol. 57-75 118 (1986)).
   (2) Fragmentation of Chromosomal DNA
   The obtained pure chromosomal DNA was placed in a DNA fragmentation device HydroShear (Tomy Digital Biology Co., Ltd.) so as to form the chromosomal DNA into fragments of about 1-2 kb.
   (3) End Treatment of Fragmented DNA
   The fragmented chromosomal DNA was treated with BAL31 nuclease (Takara Shuzo Co. Ltd.) and then the end thereof was blunted by a treatment by a Klenow Fragment (Takara Shuzo Co. Ltd.).
   (4) Addition of Adaptor to the End
   To both ends of the end-blunted chromosomal DNA fragment, an adaptor including (P) 5'-CGAGAGCGGC-CGCTAC-3' and (P) 5'-GTAGCGGCCGCTC-3' was ligated by using T4 DNA Ligase (Takara Shuzo Co. Ltd.).

2. Transformation
   After pUC19 was cut with a restriction enzyme SalI (Takara Shuzo Co. Ltd.), dT was inserted into the part cut with SalI by using Taq DNA polymerase (Roche Diagnostics K. K.). The thus produced plasmid was dephospholylated by a treatment using Alkaline Phosphatase (Takara Shuzo Co. Ltd.) and used as a vector. The vector and the above produced chromosomal DNA fragment were ligated to each other by using T4 DNA Ligase and transformation was conducted by electroporation in *Escherichia coli* DH10B (Gibco).

3. Determination of Base Sequence
   The full length of the insertion fragment of the plasmid DNA including a site where a sequencing primer was annealed was amplified by culturing *Escherichia coli* transformant in a 2xYP medium at 37° C. for 10 hours so as to collect fungi, followed by heat-treating in sterile water at 99° C. for 10 minutes so as to obtain a supernatant; and carrying out PCR using the supernatant 30 cycles of reactions at 98° C. for 20 seconds and at 68° C. for 2 minutes. The obtained DNA fragment was used as template for Sangaer method so as to carry out a sequence reaction by using a PRISM Dye-Terminator Sequencing Kit (Perkin Elmer) and in accordance with the instruction attached to the kit. Sequence reaction product was subjected to gel filtration so as to remove unreacted Dye-terminator and thereafter the base sequence of DNA fragment was decoded by using 3700 DNA Sequencer (PerkinElmer). Waveform data output from the 3700 DNA Sequencer was analyzed again by using Phred (Phil Green), vector and adaptor sequences were removed, followed by assembling by SPS Phrap (Southwest Parallel Software Inc.) so as to construct Contig sequence of *Aspergillus* genome DNA base sequence.

EXAMPLE 2

Identification of Gene

Identification of gene from a genome DNA base sequence was conducted by the following technique. In the technique of identifying genes, with respect to the contig sequence of the genome DNA base sequence, the combination of a gene region prediction system GeneDecoder based on algorithm by Kiyoshi Asai et al. (Pacific Symposium on Biocomputing 98, 228-239) and a gene region prediction system ALN based on algorithm (Bioinformatics 2000 16: 190-202) by Osamu Goto was used while considering the homology between sequence information on the already obtained ESTs and amino acid sequence databases of the well-known protein. Furthermore, for predicting a tRNA gene, tRNA-scan was used.

<1> "Extraction of BLAST Homologous Gene Candidate Region"

A region having a high homology to the amino acid sequence of the known protein was extracted from the contig sequence of the genome DNA base sequence. The homology of amino acid sequence can be determined by algorithm BLAST by Karlin and Altschul (Proc. Natl. Acad. Sei. USA 87:2264-2268, 1990, Proc. Natl. Acad. Sei. USA 90:5873-5877, 1993). Based on this algorithm, a program called BLASTX was developed (Altschul et al. J. Mol. Biol. 215:403-410, 1990). A region having high homology, when the genome DNA base sequence is translated into the amino acid sequence, can be directly retrieved by the BLASTX. The specific technique of these analysis methods is well known (http://www.ncbi.nlm.nih.gov). In this technique, by searching the BLASTX under the conditions that the contig sequence of the genome DNA base sequence is used as a query sequence and that SWISSPROT version 39 (Bairoch, A. & Apweiler, R. Nucleic Acids Res. 28, 45-48 (2000).) and NRaa are used as databases, and then a region having an E-value (i.e., index of homology in BLAST algorithm) of $10^{-30}$ or less is extracted (note here that as the E-value is small, the homology is high). From these regions, BLAST homologous gene candidate regions are extracted by giving high priority to a part having high homology so that the candidate regions are not overlapped with each other.

<2> "Extract of ALN Gene Candidate Region"

Among the BLAST homologous gene candidate regions, a region having homology with respect to 90% or more of the full length of the amino acid sequence of the protein that is a subject of homology is made to be core, and an ALN gene candidate region is extracted by applying a gene region prediction system ALN with respect to the contig sequence. The ALN predicts a gene region by identifying a splice site while aligning the full length of an amino acid sequence of the protein that is a subject of homology with respect to the contig sequence.

<3> "Extraction of GD Homologous Gene Candidate Region"

Among the BLAST homologous gene candidate regions, a region having homology with respect to 20% or more and less than 90% of the full length of an amino acid sequence of the protein that is a subject of homology is made to be core, and a GD homologous gene candidate region is extracted by applying a gene region prediction system GeneDecoder with respect to the contig sequence. GeneDecoder predicts a gene region by integrating E-value of BLASTX and statistic amount of 2 series of codons (index of direction of the protein coding region) and further considering a score by a position-dependent primary Markov Model of the splice site.

<4> "Extraction of EST-GD Gene Candidate Region"

As to a region in which gene expression is confirmed by EST corresponding to the contig sequence, by applying GeneDecoder to the contig sequence in the vicinity of the region, not only a gene region determined by EST sequence but also an entire region of gene is predicted. Thus, an EST-GD gene candidate region is obtained.

<5> "Extraction of General GD Gene Candidate Region"

With respect to the contig sequence that is not included in <1> to <4> mentioned above, by applying GeneDecoder, gene a region is predicted.

<6> Extraction of tRNA Gene Candidate Region"

By applying tRNA-scan to the entire contig sequence, a tRNA gene region candidate region is extracted.

<7> "Integration of Gene Candidate Regions"

By the following procedures, gene candidate regions described in the above <2> to <6> are integrated. Firstly, in the gene candidate regions <2> to <6>, a gene region that is expected to have gene regions which are contradictory to the splice site determined by EST are removed. The rest of the gene candidate regions are integrated with the regions overlapped with each other excluded. At this time, tRNA, ALN homologous gene candidate region, GD homologous gene candidate region, GD-EST gene candidate region, general GD gene candidate region are integrated by giving a higher priority in this order. This integrated gene candidate regions are made to be a set of the prediction genes.

By the above-mentioned procedures, from the viewpoint of homology, a gene having homology over the full length of the well-known protein, a gene having homology to a part of the well-known protein, and a gene having no homology to the well-known protein are ensured to be identified with higher reliability in this order. Furthermore, from the viewpoint of confirmation of expression, a gene whose expression is confirmed by EST and a gene whose expression is not confirmed by EST are identified with reliability in this order. Furthermore, all the candidate genes are ensured that they are not contradictory to the splice site identified by EST.

The technique used employs algorithm that is not allowed to contain a stop codon in a protein encoding region, so that there is little possibility of predicting a pseudogene as a gene.

As to determination of functions, with respect to the predicted gene region, the database Nraa in BLAST is searched for homology, and the function is determined with a sufficient homology (E-value: $10^{-30}$) as a threshold value.

EXAMPLE 3

Retrieving for Sequence Encoding Lysyl Oxidase

As result of Example 2, sequences having a certain function (function sequences) were predicted and extracted from *Aspergillus* genome DNA. Among these function sequences, for all of the sequences that were anticipated to encode proteins, BLAST search (Standard protein-protein BLAST: blastp) provided by NCBI was used to retrieve a region having high homology to a lysyl oxidase gene derived from *Pichia Pastoris*. As a result, the high homology to a lysyl oxidase gene derived from *Pichia Pastoris* was successfully found in a sequence set force in SEQ ID NO: 24 (the sequence contains a sequence (SEQ ID NO: 8) as shown by SEQ ID NO: 36845 in the prior application). Thus, for the purpose of analyzing the function of the region and identifying an amino acid sequence of the protein encoded by the region, the following various experiments were conducted.

EXAMPLE 4

Obtaining Chromosomal Gene

*Aspergillus oryzae* RIB-40 strain was cultured over night at 30° C. by using a Sakaguchi flask containing 100 ml of a potato dextrose medium (Difco). Then, the medium solution was filtrated by using a Buchner funnel and Nutsche suction bottle so as to obtain fungus bodies. The fungus bodies were washed with 300 ml of water, frozen at −80° C. and then freeze-dried. As a result, about 0.3 g of the obtained fungus bodies were ground together with one spoonful of sea sand with the use of a mortar and a pestle, followed by suspending in 8 ml of TE solution (10 mM of Tris-HCl (pH 8.0) and 1 mM EDTA). To the suspension, 4 ml of 10% SDS aqueous solution was added and stirred vigorously. Then, the equal amount of phenol:chloroform:isoamyl alcohol (25:24:1) solution was added and stirred, followed by centrifugation (1500 g, 5 minutes, at room temperature) to obtain a supernatant. To the supernatant, 100 µl of TE solution containing 20 mg/ml of Proteinase K (Roche Diagnostics K.K.) was added and stirred, followed by incubating at 37° C. for 30 minutes. Then, the equal amount of phenol:chloroform:isoamyl alcohol solution was added again and stirred, followed by centrifugation (1500 g, 5 minutes, at room temperature) so as to obtain supernatant. To the obtained supernatant, the equal amount of isopropanol was added gently. With this treatment, chromosomal DNA precipitating on the interface was reeled up with the use of a Pasteur pipette. The chromosomal DNA was washed with 70% ethanol and air-dried. The thus obtained chromosomal DNA was dissolved in 3 ml of TE solution again to which 100 µl of 10 mg/ml RNase A (SIGMA) was added, followed by incubating at 37° C. for 30 minutes. Then, 25 µl of 20 mg/ml of Proteinase K solution was added and stirred, followed by incubating at 37° C. for 30 minutes. Then, the equal amount of phenol:chloroform:isoamyl alcohol (25:24:1) solution was added. After stirring, centrifugation (1500 g, 5 minutes, at room temperature) was conducted so as to obtain a supernatant. After repeating this washing operation twice, to the obtained supernatant, the equal amount of chloroform: isoamyl alcohol (24:1) solution was added and stirred, followed by centrifugation (1500 g, 5 minutes, at room temperature) to obtain a supernatant. To the obtained supernatant, 1/10 volume of 3 M NaOAc (pH 4.8) and two-times volume of ethanol were added and cooled at −80° C. so as to precipitate chromosomal DNA. The precipitated chromosomal DNA was collected by centrifugation (1500 g, 5 minutes, at room temperature). The collected chromosomal DNA was washed with 70% ethanol, vacuum dried, and finally dissolved in 300 µl of TE solution to obtain a chromosomal DNA solution with the concentration of about 1 mg/ml.

EXAMPLE 5

Production of Probe for Colony Hybridization

Based on sequence information on the contig sequence of the *Aspergillus* genome DNA obtained in Example 1, a primer pair, which amplifies a genome DNA fragment which exists in a restriction enzyme BalI fragment (SEQ ID NO: 24) and contains a part of a region of the targeted gene (putative lysyl oxidase gene), was designed as follows.

```
LO-2:
5'-TAGCACCATCTACTCTGAGTGGC-3'    (SEQ ID NO: 11)

LOR-2:
5'-CCTGGTCATATAGTCGTAGTTGC-3'    (SEQ ID NO: 12)
```

By using this primer pair, PCR was conducted. Note here that the composition of the reaction solution was as follows.
sterile water: 36.75 µl
10× Buffer for Pyrobest® DNA Polymerase: 5 µl
2.5 MI dNTP solution: 4 µl
10 pmol/µl LO-2: 1 µl
10 pmol/µl LOR-2: 1 µl
60 ng/µl RIB40 chromosomal DNA: 2 µl
5 U/µl Pyrobest® DNA Polymerase (Takara Shuzo Co. Ltd.): 0.25 µl/50 µl To the above-mentioned reaction solution, 50 µl of mineral oil was dropped and PCR was conducted by using GeneAmp™ PCR System PJ9600 (PE Bio System) under the following conditions.

(1) Reaction at 94° C. for minute, (2) 30 cycles of reactions at 94° C. for 30 seconds, at 50° C. for 30 seconds and at 72° C. for 2 minutes, and (3) allowed to stand at 4° C.

As a result of PCR, about 900 bp of DNA fragment was specifically amplified and the amplified DNA fragment was extracted by using GeneCleanIII (BIO 101) after carrying out Agarose gel electrophoresis. The extracted DNA fragment was subcloned into pUC19, and then inserted DNA fragment was DIG labeled with DIG High Prime (Roche Diagnostics K.K.) so as to obtain a probe of putative lysyl oxidase gene.

EXAMPLE 6

Colony Hybridization

40 µg of chromosomal DNA obtained in Example 4 was completely digested at 37° C. with the use of 50 U restriction enzyme BalI (Takara Shuzo Co. Ltd.). Then, a DNA fragment having a chain length of 9.1 kbp was cut out by Agarose electrophoresis, and then extracted with the use of GeneCleanIII (BIO 101) so as to make an insert for producing library. On the other hand, after pUC19 was completely digested (incubation at 30° C. for one night) by using 80 U SmaI (Takara Shuzo Co. Ltd.), followed by dephosphorylation with the use of alkaline phosphatase (Takara Shuzo Co. Ltd.) so as to make a vector for producing library. The thus prepared insert DNA and vector DNA were ligated to each other with the use of Ligation Kit ver.2 (Takara Shuzo Co. Ltd.), which was used so as to transform *Escherichia coli* DH5 strain Competent Cell (TOYOBO). Ampicillin resistance transformation strains were inoculated so that about 200 colonies were formed for one sheet of LA plate (ampicillin (SIGMA) 100 µg/ml) and incubated at 37° C. for one night so as to grow colonies. The grown colonies (total number: about 4000) were lifted to Nylon Membranes for Colony and Plaque Hybridization (Roche Diagnostics K.K.) and DNA was immobilized on a membrane. By using the probe produced in Example 5, colony hybridization was conducted so as to detect colonies showing strong signal with the use of DIG Nucleic Acid Detection Kit (Roche Diagnostics K.K.). As a result of the colony hybridization, a plasmid carried by the selected clone was called pULO so as to make it a plasmid containing a putative lysyl oxidase gene. Note here that each of the above-mentioned operations was conducted in accordance with the protocol attached to the reagent or kit.

EXAMPLE 7

Analysis of Base Sequence of Clone Containing Putative Lysyl Oxidase Gene

Based on the information of a sequence (SEQ ID NO: 24: BalI fragment (the sequence includes a putative promoter region and a putative terminator region)) including a region that is expected to encode lysyl oxidase, which were clarified in Examples 1 to 3, the following 10 kinds of synthetic primers were produced, and by using these primers, a base sequence of the insert of the clone pULO was determined. For the sequence reaction, BigDye™ Terminator Cycle Sequencing FS Ready Kit VER.2 (Applied Biosystem) was used; and for analysis, ABI PRISM 310 Sequencer (Applied Biosystem) was used.

```
L-1:    5'-GCTAGCTTATACTAACCC-3'   (SEQ ID NO: 13)

L-2:    5'-GACTATGTTCTCGTGCGC-3'   (SEQ ID NO: 14)

L-3:    5'-TCTTTGCATTTGTCCAGG-3'   (SEQ ID NO: 15)

L-4:    5'-TCTGCGTCGTTGGACAAC-3'   (SEQ ID NO: 16)

L-5:    5'-GACTGACCCTCATTATGC-3'   (SEQ ID NO: 17)

L-6:    5'-AACACCGAGGGACCATGG-3'   (SEQ ID NO: 18)

L-7:    5'-TACCTCACCCTCCGATCC-3'   (SEQ ID NO: 19)

L-8:    5'-GGGACAGCACACCTGACG-3'   (SEQ ID NO: 20)

L-9:    5'-AACCCGAATGATCCGTAC-3'   (SEQ ID NO: 21)

L-10:   5'-AGAGAATAATCGAAATGG-3'   (SEQ ID NO: 22)
```

A part of the determined base sequence was perfectly identical to a sequence set forth in SEQ ID NO: 8 (a sequence including a structural gene of putative lysyl oxidase as well as a promoter and a terminator). Therefore, it was found that the plasmid pULO had a DNA fragment perfectly covering the sequence set forth in SEQ ID NO: 8 (sequence including a putative promoter, a putative structural gene and putative terminator).

EXAMPLE 8

Construction of Expression Vector pBALO

Next, 3 µg of pULO was digested with a restriction enzyme BglII (Takara Shuzo Co. Ltd.) so as to obtain about 7.0 kbp DNA fragment (SEQ ID NO: 10. Hereinafter, the fragment will be referred to as "putative lysyl oxidase DNA fragment"). The end of the obtained DNA fragment was blunted with the use of T4 DNA Polymerase (Takara Shuzo Co. Ltd.) so as to make it an insert DNA. On the other hand, 7.5 g of expression vector pBAR in which ArgB gene derived from *Aspergillus nidulans* was inserted into SalI-XoI site of pBluescript II KS (+) was completely digested (incubated at 30° C. for one night) with the use of 80 U of SmaI (Takara Shuzo Co. Ltd.). Thereafter, with the use of Alkaline Phosphatase (Takara Shuzo Co. Ltd.), dephosphorylation was conducted so as to make a vector DNA. The insert DNA and the vector DNA, which were prepared as mentioned above, were ligated to each other with the use of Ligation Kit ver.2 (Takara Shuzo Co. Ltd.), thereby transforming *Escherichia coli* DH5 strain competent cell (TOYOBO) to obtain ampicillin resistant transformant. The plasmid carried by the obtained clone was called pBALO and used as an expression vector (see FIG. 1).

EXAMPLE 9

Transformation of *Aspergillus nidulans*

*Aspergillus nidulans* ABPU1 strain (ornithine carbamoyltransferase gene defective strain of *Aspergillus nidulans*) that is auxotrophic mutant was cultured at 37° C. for one night under the following medium conditions.

<Complete Medium>
  malto extract: 20 g
  glucose: 20 g
  bactopeptone: 1 g
  uridine: 2 g
  p-amino benzoic acid: 2.5 mg
  riboflavine: 2.5 mg
  pyridoxine: 2.5 mg
  biotin: 2.5 mg
  arginine hydrochloride: 055 g/L (pH 6.5)

Fungus bodies collected from 200 ml of culture medium obtained by culturing under the above-mentioned conditions and then collecting with the use of a glass filter (100 μm) was suspended in a protoplast preparation solution having the following compositions.
  sterile MillQ water: 37 ml
  sodium chloride: 1.9 g
  0.4 M sodium phosphate solution (pH 5.8): 1 ml
  1 M calcium chloride aqueous solution: 0.8 ml
  Novozyme 234 (NOVO NORDISK): 150 mg/40 ml (aseptic filtration by cellulose nitrate filter (0.45 μm))

The above-mentioned suspension was treated for 1 protoplastization at 30° C. at 78 rpm for one hour. The obtained protoplast suspension was filtrated with a nylon filter (230-mesh) and the filtrate was centrifuged (400 g, 5 minutes, at room temperature) so as to obtain protoplast. 10 ml of the protoplast was washed with 0.8 M NaCl, and then centrifuged (400 g, 5 minutes, at room temperature) so as to obtain precipitates of protoplast. The obtained protoplast precipitate was suspended in 200 μl of 0.8 M NaCl-50 mM CaCl$_2$ to obtain a protoplast solution. The concentration of protoplast was calculated by the observation through microscope. By using the protoplast suspension diluted to $2 \times 10^8$/ml, the transformation was conducted in accordance with the following procedure. 5 μl of pBALO solution (3 μg/μl) was added and suspended in 50 μl protoplast suspension, and then 12.5 μl of PEG solution (25% PEG6000, 50 mM CaCl$_2$ and 10 mM Tris-HCl (pH 7.5)) was added and further suspended, and allowed to stand in ice for 20 minutes. Then, 500 μl of PEG solution (25% PEG6000, 50 mM CaCl$_2$, 10 mM Tris-HCl (pH 7.5)) was added and suspended again, and allowed to stand in ice for 5 minutes. Finally, 1 ml of 0.8 M NaCl-50 mM CaCl$_2$ was added and suspended. 0.5 ml of suspension solution was placed in a schale and then the following regenerated medium was poured thereto so as to solidify it as a plate. It was incubated at 37° C. for 3-4 days and a single fungus was isolated in the below-mentioned minimum medium so as to obtain a transformant strain into which a putative lysyl oxidase DNA fragment was introduced.

<Regenerated Medium>
  sodium nitrate: 6 g
  potassium phosphate: 1.52 g
  potassium chloride: 0.52 g
  sorbitol: 218.6 g
  uridine: 2.0 g
  p-amino benzoic acid: 2.5 mg
  riboflavine: 2.5 mg
  pyridoxine: 2.5 mg
  biotin: 2.5 mg
  agar: 20 g/L (pH 6.5)

(the following materials were added after sterilization (121° C., 20 minutes))
  50% glucose: 20 ml
  5.2% magnesium sulphate-7-hydrate: 10 ml <Minimum Medium>
  sodium nitrate: 0.85 g
  potassium phosphate: 1.525 g
  potassium chloride: 0.525 g
  Trace element: 1.5 ml
  Uridine: 2 g
  p-amino benzoic acid: 2.5 mg
  riboflavine: 2.5 mg
  pyridoxine: 2.5 mg
  biotin: 2.5 mg
  agar: 15 g/L (pH 6.5)

(the following materials were added after sterilization (121° C., 20 minutes))
  50% glucose: 20 ml
  5.2% magnesium sulphate-7-hydrate: 10 ml <Trace Element>
  4-sodium borate-10-hydrate: 40 mg
  copper sulfate-5-hydrate: 0.4 g
  iron sulfate-7-hydrate: 1.6 g
  manganese sulfate-4-hydrate: 0.8 g
  sodium molybdate-2-hydrate: 0.8 g
  zinc sulfate-7-hydrate: 8 g/L

EXAMPLE 10

Culture of Transformant

The transformant was culture while shaking at 30° C. for 3 days under the following conditions.

<SPY medium+vitamins>
  starch: 30 g
  polypeptone: 10 g
  yeast extract: 5 g
  potassium chloride: 2 g
  potassium phosphate: 1 g
  residues of alcohol fermentation: 0.1 g
  uridine: 2 g
  p-amino benzoic acid: 2.5 mg
  riboflavine: 2.5 mg
  pyridoxine: 2.5 mg
  biotin: 2.5 mg (the following materials were added after sterilization (121° C., 20 minutes))
  5.2% magnesium sulphate-7-hydrate: 10 ml/L (pH 6.5)

The culture medium (10 ml) cultured under the above-mentioned conditions was centrifuged (2,400 g, 10 minutes, 4° C.) so as to obtain a culture supernatant.

EXAMPLE 11

Measurement of Enzyme Activity of Lysyl Oxidase

By using each of the obtained culture supernatants, the lysyl oxidase activity was measured in accordance with the following procedures. For a control, a culture supernatant obtained by similarly culturing *Aspergillus nidulans* ABPU1 strain, which had not been transformed, in a medium obtained by adding arginine hydrochloride into the above-mentioned medium to the concentration of 0.55 g/L was used.

The lysyl oxidase activity was calculated from the produced amount of dimmer generated by the polymerization of allicin and lysine which were generated after the substrate lysine was oxidized by lysyl oxidase. The amount of lysine dimmer was measured by using LC-MS (Agilent).

Firstly, by using each culture supernatant (crude enzyme sample), the following reaction solution was prepared.

0.1 M potassium phosphate buffer (pH 7.0): 235 µl
1.0 M lysine hydrochloride aqueous solution: 60 µl
culture supernatant: 6 µl
total: 301 µl Each reaction solution was incubated at 37° C., and 30 µl each of reaction solution was sampled after 1, 2, 4, 8 and 24 hours, respectively. The sampled reaction solution was subjected to heat treatment at 100° C. for 15 minutes and the reaction was stopped. Then a LC mobile phase was used so as to dilute 10 times and a sample to be measured was obtained. Note here that a sample obtained by using a culture supernatant in which the enzyme had been inactivated by a heat treatment at 100° C. for 15 minutes in advance was used as a blank.

For measuring the amount of lysine dimmer in each measurement sample, Agilent 1100 series LC/MSD system (Agilent) was used. As a separation column, supelco ABZ plus (Spelco) was used. Value obtained by subtracting a blank sample value from a peak area value of the ratio of mass to charge (m/Z) 275 detected as a peak of lysine dimmer in the positive mode was made to be a measurement value of each sample.

Figure 2:
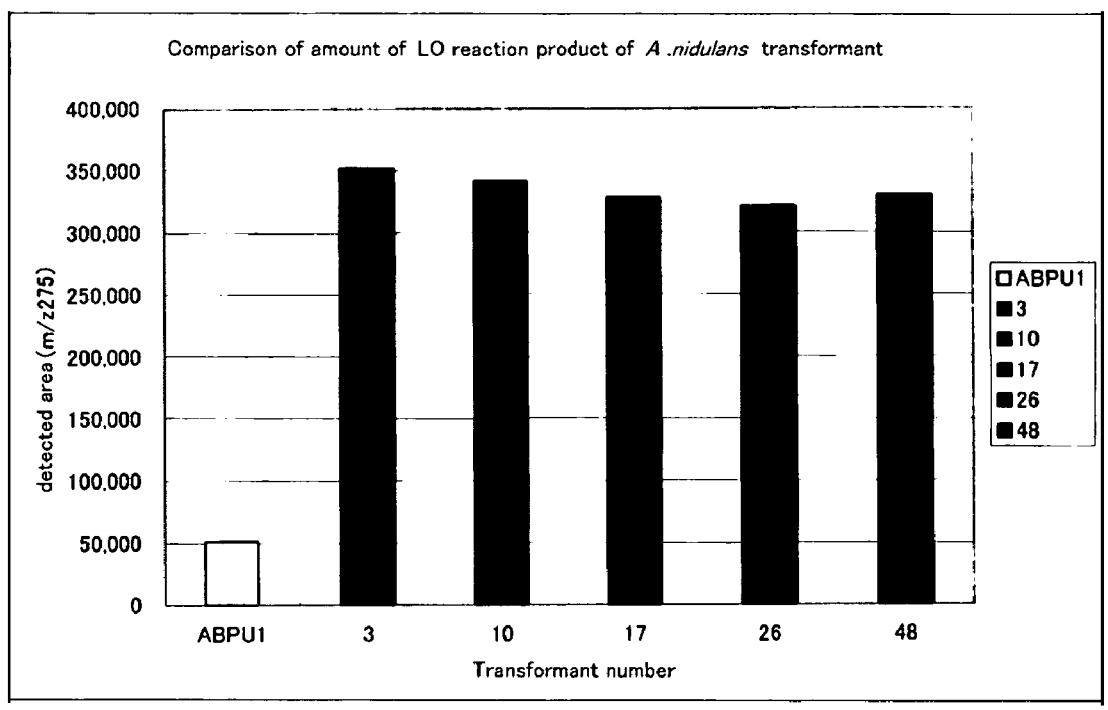
FIG. 2 is a table (upper part) and a graph (lower part) showing measurement results of the activity of lysyl oxidase using filamentous fungi transformed by the vector pBALO. ABPUI1 represents a control (a sample using a culture supernatant of *Aspergillus nidulans* ABPU1 strain).

As a result of measurement, in some samples using culture supernatant of transformant, it was found that the measurement value was increased in proportion to the reaction period of time. That is to say, it was found that the amount of lysine dimmer was increased in proportion to the reaction time. The measurement results using measurement sample whose reaction period of time was 24 hours are shown in table and graph in FIG. 2. Note here that only the result of the sample whose amount of lysine dimmer was confirmed to be increased was extracted to be shown. As is apparent from the table and graph, in samples using the culture supernatant of transformant L-3, 10, 17, 26 and 48, respectively, the activity having not less than 6 times higher than that of a control (ABPU1 strain) was shown. Thus, it was confirmed that these transformants had a lysyl oxidase gene.

The above-mentioned results demonstrated that putative lysyl oxidase DNA fragment used for producing transformant contained a region encoding lysyl oxidase.

EXAMPLE 12

Determination of Transcription Termination Point of Gene

*Aspergillus oryzae* RIB-40 strain and the transformant LO-3 (*Aspergillus nidulans* ABPU1) which exhibited the maximum lysyl oxidase activity in the above activity measurement were cultured in the same manner as in Example 10 so as to prepare fungus bodies. From the obtained fungus bodies, all RNAs were extracted by Trisol reagent (GIBCO BRL). By using the RNAs as templates, a 3'DNA fragment was amplified by using 3'-Full RACE Core Set (Takara Shuzo Co. Ltd). Specific sequence in a synthetic primer designed from the information of lysyl oxidase genome to be used is shown below.

LO-3':
5'-TGGCTGAACCTGGGGATGCACCAC-3'  (SEQ ID NO: 23)

As a result of analysis of base sequence of the amplified DNA fragment, the base sequence (SEQ ID NO: 9) of the DNA fragment was identical to a part of the base sequence of a region that was anticipated to be a structural gene of the original lysyl oxidase in Examples 1 to 3 and had poly A sequence. It was found from these facts that the DNA fragment was a DNA fragment showing 3' end of the putative lysyl oxidase structural gene. Thus, the transcription termination point of the putative lysyl oxidase structural gene was clarified and it was found that it was positioned at the side of 3' terminal. Thus, the transcription termination point of a structural gene of the putative lysyl oxidase was clarified and turned to be positioned closer to the side of 3' end than expected. That is to say, from the above-mentioned results, it was found that the sequence of a structural gene obtained from the above-mentioned results differed in the 3' end region from the originally identified sequence as a structural gene. Note here that a structural gene newly identified based on the above-mentioned results and an amino acid sequence thereof are respectively shown in SEQ ID NO: 3 and SEQ ID NO: 2.

EXAMPLE 13

Construction of Expression Vector Carrying Insert DNA Having Deletion in 3' Side Region From the result in Example 12, it was clarified that about 7.0 kbp insert DNA which had been inserted into the expression vector pBALO had a region unnecessary to lysyl oxidase activity in its 3' region. Then, for the purpose of narrowing a region necessary to lysyl oxidase activity, an insert DNA in which a part of 3' side of the insert DNA was deleted (hereinafter, referred to as "deleted insert DNA"). 3 µg of pBALO was digested with restriction enzymes AccIII and AflII (Takara Shuzo Co. Ltd) and divided into about 2.2 kbp region at the side of 3' side region which was thought to be unnecessary to expression and about 9.4 kbp vector fragment containing a deletion insert DNA. Then, only the vector fragment was extracted and the end thereof was end-blunted with T4 DNA Polymerase (Takara Shuzo Co. Ltd), followed by self-ligation with the use of a Ligation Kit ver.2 (Takara Shuzo Co. Ltd). By using the thus obtained expression vector, *Escherichia coli* DH5 strain (TOYOBO) was transferred and an ampicillin resistant transformant was selected. A plasmid carrying the selected clone was named pBALO-D and used for the following experiment as a new expression vector (see FIG. 4).

EXAMPLE 14

Obtaining of Transformant and Measurement of Lysyl Oxidase Activity

Figure 5:
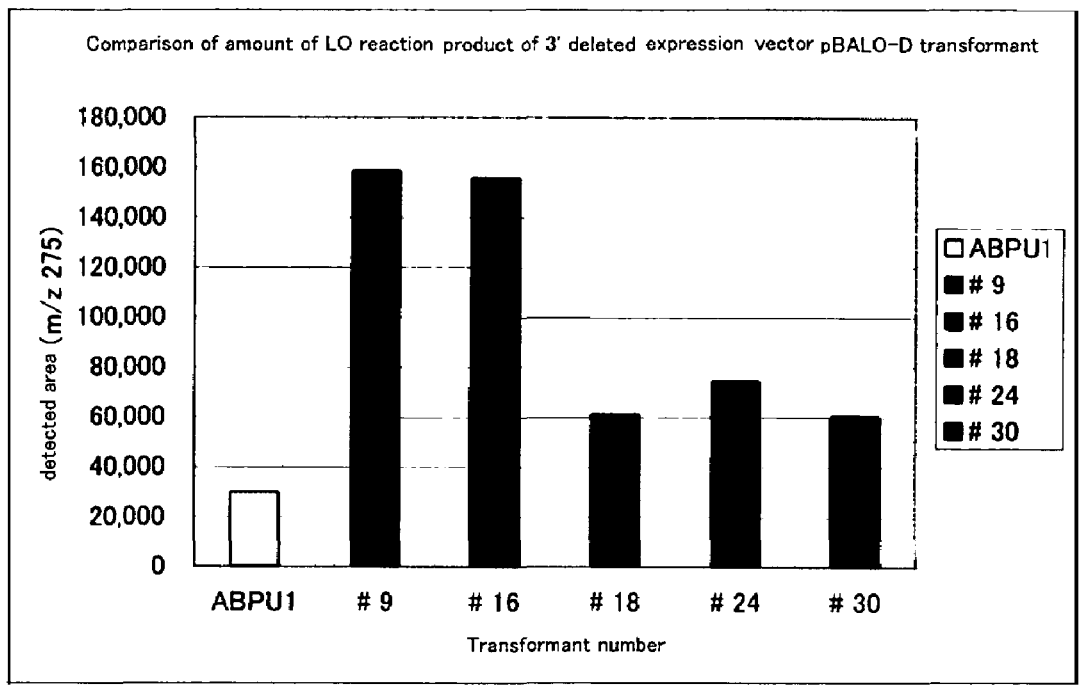
FIG. 5 is a table (upper part) and a graph (lower part) showing measurement results of the activity of lysyl oxidase using filamentous fungi transformed by the vector pBALO-D. ABPUI1 represents a control (a sample using a culture supernatant of *Aspergillus nidulans* ABPU1 strain).

The measurement of lysyl oxidase activity of the transformant into which pBALO-D was introduced in accordance with the procedures the same as in Examples 9 to 11. FIG. 5 shows the measurement results when measurement samples whose reaction period was 8 hour were used. Note here that only the results of samples whose amount of lysine dimer was confirmed to be increased was extracted to be shown. As is apparent from these table and graph, similar to the results in Example 11, transformants LOD-9, 16 exhibiting the activity that was not less than 5 times higher than that of a control (ABPU1 strain) were obtained. From these results, it was confirmed that pBALO-D carried a lysyl oxidase gene capable of expressing. Therefore, it was found that a deletion insert DNA (SEQ ID NO: 1) carried by pBALO-D had a sequence necessary to expression of lysyl oxidase gene. As mentioned above, a minimum region necessary to expression of the lysyl oxidase gene was further identified by this Example.

The present invention is not particularly limited to the above-mentioned embodiments of the present invention and descriptions of Examples. Variations which are within the scope of the following claims and which a person skilled in the art can achieve easily are also included in the present invention.

INDUSTRIAL APPLICABILITY

According to the present invention, lysyl oxidase derived from filamentous fungi and DNA encoding thereof are provided. By using the DNA of the present invention, a production system of lysyl oxidase using filamentous fungi with high safety is constructed.

The invention claimed is:

1. An isolated lysyl oxidase consisting of a protein described in the following (a) or (b):
   - (a) a protein having the amino acid sequence set forth in SEQ ID NO: 2, or
   - (b) a protein having an amino acid sequence obtained by modifying 5% or less of the amino acids of the amino acid sequence set forth in SEQ ID NO: 2, and functioning as lysyl oxidase.

2. An isolated DNA described in the following (A) or (B):
   - (A) a DNA encoding the lysyl oxidase described in claim 1; or
   - (B) a DNA which hybridizes under stringent conditions of 50% formamide, 10×SSC, 5×Denhardt solution, 1% SDS, 10% dextran sulfate, 10 µg/ml denatured salmon sperm DNA, 50 mM phosphate buffer (pH 7.5) at 42° C., to the full length complement of (A) and encoding a protein which functions as a lysyl oxidase.

3. An isolated DNA having any one of the following sequences (i) to (vi):
   - (i) a nucleotide sequence of SEQ ID NO: 3;
   - (ii) a nucleotide sequence of SEQ ID NO: 4;
   - (iii) a nucleotide sequence of SEQ ID NO: 5;
   - (iv) a nucleotide sequence of SEQ ID NO: 6;
   - (v) a nucleotide sequence of SEQ ID NO: 1; and
   - (vi) a nucleotide sequence of SEQ ID NO: 7.

4. A vector comprising the DNA described in claim 2.

5. A vector comprising the DNA described in claim 3.

6. Filamentous fungi into which the DNA described in claim 2 is exogenously introduced.

7. Filamentous fungi into which the DNA described in claim 3 is exogenously introduced.

8. A method for producing lysyl oxidase, the method comprising the following steps (1) and (2):
   - (1) a step of culturing the filamentous fungi described in claim 6 under conditions where a protein encoded by the DNA can be produced; and
   - (2) a step of collecting the produced product.

9. A method for producing lysyl oxidase, the method comprising the following steps (1) and (2):
   - (1) a step of culturing the filamentous fungi described in claim 7 under conditions where a protein encoded by the DNA can be produced; and
   - (2) a step of collecting the produced protein.

* * * * *